(12) United States Patent
Eisenthal et al.

(10) Patent No.: US 12,193,651 B2
(45) Date of Patent: Jan. 14, 2025

(54) APPARATUS AND METHOD TO SEAL A TISSUE TRACT

(71) Applicant: PneumoNix Medical, Inc., Brooklyn, NY (US)

(72) Inventors: Andrew Eisenthal, Baltimore, MD (US); Edward Ruppel, III, Baltimore, MD (US); Shashwat Gupta, Baltimore, MD (US)

(73) Assignee: PNEUMONIX MEDICAL, INC., Brooklyn, NY (US)

( * ) Notice: Subject to any disclaimer, the term of this patent is extended or adjusted under 35 U.S.C. 154(b) by 28 days.

(21) Appl. No.: 18/123,024

(22) Filed: Mar. 17, 2023

(65) Prior Publication Data

US 2023/0404550 A1    Dec. 21, 2023

Related U.S. Application Data

(63) Continuation of application No. 16/767,214, filed as application No. PCT/US2018/062799 on Nov. 28, 2018, now Pat. No. 11,638,578.

(60) Provisional application No. 62/591,193, filed on Nov. 28, 2017, provisional application No. 62/721,924, filed on Aug. 23, 2018.

(51) Int. Cl.
| | | |
|---|---|---|
| *A61B 10/00* | (2006.01) | |
| *A61B 10/02* | (2006.01) | |
| *A61B 17/00* | (2006.01) | |
| *A61B 90/00* | (2016.01) | |

(52) U.S. Cl.
CPC .... *A61B 10/0233* (2013.01); *A61B 17/00491* (2013.01); *A61B 17/0057* (2013.01); *A61B 90/39* (2016.02); *A61B 2017/00367* (2013.01); *A61B 2017/0065* (2013.01); *A61B 2017/00809* (2013.01); *A61B 2090/3966* (2016.02)

(58) Field of Classification Search
CPC ............... A61B 10/0233; A61B 90/39; A61B 17/00491; A61B 17/0057; A61B 2090/3966; A61B 2017/00367; A61B 2017/0065; A61B 2017/00809
See application file for complete search history.

(56) References Cited

U.S. PATENT DOCUMENTS

| | | |
|---|---|---|
| 3,330,268 A | 7/1967 | Goldsmith |
| D250,544 S | 12/1978 | Leonard |
| D269,549 S | 6/1983 | Gross |
| D286,677 S | 11/1986 | Osborne |
| 4,670,008 A | 6/1987 | Von Albertini |
| 5,256,149 A | 10/1993 | Bank et al. |
| D342,136 S | 12/1993 | Lafferty et al. |
| D353,668 S | 12/1994 | Banks et al. |

(Continued)

FOREIGN PATENT DOCUMENTS

| | | |
|---|---|---|
| EP | 0858776 A2 | 8/1998 |
| KR | 101151310 B1 | 6/2012 |

(Continued)

OTHER PUBLICATIONS

International Application No. PCT/US2020/035851, International Search Report and Written Opinion mailed Aug. 19, 2020, 8 pages.

(Continued)

*Primary Examiner* — Steven O Douglas
(74) *Attorney, Agent, or Firm* — Patrick J. Halloran

(57) ABSTRACT

The invention relates to a device and method for blocking air contributing to pneumothorax during a lung biopsy.

13 Claims, 30 Drawing Sheets

(56) References Cited

U.S. PATENT DOCUMENTS

| | | |
|---|---|---|
| 5,387,197 A | 7/1995 | Smith et al. |
| 5,437,631 A | 8/1995 | Janzen |
| 5,571,133 A | 11/1996 | Yoon |
| D379,515 S | 5/1997 | Kuehn et al. |
| 6,045,570 A | 4/2000 | Epstein et al. |
| 6,685,727 B2 | 2/2004 | Fisher et al. |
| 6,692,467 B2 | 2/2004 | McFarlane |
| 6,770,070 B1 | 8/2004 | Balbierz |
| 6,790,185 B1 | 9/2004 | Fisher et al. |
| 6,840,952 B2 | 11/2005 | Saker et al. |
| D582,552 S | 12/2008 | Berberich |
| 7,766,891 B2 | 8/2010 | McGurk et al. |
| D624,653 S | 9/2010 | Boillat |
| D630,734 S | 1/2011 | Spieser |
| 8,029,474 B2 | 4/2011 | Chung |
| D640,785 S | 6/2011 | Lee |
| D654,583 S | 2/2012 | Lee-Sepsick |
| D663,832 S | 7/2012 | Essinger et al. |
| D687,548 S | 8/2013 | Hayashi |
| D692,134 S | 10/2013 | Lee-Sepsick |
| D699,341 S | 2/2014 | Clark |
| D715,431 S | 10/2014 | Vonck et al. |
| D735,331 S | 7/2015 | Mastri et al. |
| D747,802 S | 1/2016 | Freigang et al. |
| D748,254 S | 1/2016 | Freigang et al. |
| D751,704 S | 3/2016 | Corydon et al. |
| D772,411 S | 11/2016 | Heath et al. |
| D785,173 S | 4/2017 | Oberkircher et al. |
| D796,042 S | 8/2017 | Eubanks |
| D831,213 S | 10/2018 | Kuun |
| D854,148 S | 7/2019 | Prinz |
| D864,388 S | 10/2019 | Barber |
| D935,611 S | 11/2021 | Eisenthal et al. |
| 2003/0097079 A1 | 5/2003 | Garcia |
| 2004/0167473 A1 | 8/2004 | Moenning |
| 2004/0236340 A1 | 11/2004 | Cirotteau et al. |
| 2004/0267308 A1 | 12/2004 | Bagaosian et al. |
| 2006/0025749 A1 | 2/2006 | Moenning |
| 2006/0025815 A1 | 2/2006 | McGurk et al. |
| 2008/0294111 A1 | 11/2008 | Tal et al. |
| 2009/0221960 A1 | 3/2009 | Albrecht et al. |
| 2011/0208157 A1 | 8/2011 | Geliebter et al. |
| 2013/0053791 A1 | 2/2013 | Clark |
| 2014/0128671 A1 | 5/2014 | Riek et al. |
| 2014/0194685 A1 | 7/2014 | Riek et al. |
| 2014/0222067 A1 | 8/2014 | Ericson et al. |
| 2015/0230868 A1 | 8/2015 | Miller |
| 2016/0120528 A1 | 5/2016 | Abtin |
| 2016/0000462 A1 | 7/2016 | Pajunk et al. |

FOREIGN PATENT DOCUMENTS

| | | |
|---|---|---|
| KR | 20150117517 A | 10/2015 |
| KR | 100786728 B1 | 12/2017 |
| WO | 2011026935 A1 | 3/2011 |
| WO | 2013000536 A1 | 1/2013 |
| WO | 2013135354 A2 | 9/2013 |
| WO | 2019108618 A1 | 6/2019 |

OTHER PUBLICATIONS

International Search Report for PCT/US18/62799 (Apr. 25, 2019).
International Preliminary Examination Report for PCT/US18/62799 (Jun. 2, 2020).

APPARATUS AND METHOD TO SEAL A TISSUE TRACT

RELATED APPLICATIONS

This application is a continuation application of U.S. Ser. No. 16/767,214 filed on May 27, 2020 that was filed under 35 U.S.C. § 371 and claims priority to International Application No. PCT/US2018/062799 filed on Nov. 28, 2018, and claims priority to U.S. Ser. No. 62/591,193 filed on Nov. 28, 2017 and U.S. Ser. No. 62/721,924 filed on Aug. 23, 2018, which are hereby incorporated by reference into this disclosure in their entirety.

FIELD OF THE DISCLOSURE

The invention relates to a device and method for blocking air contributing to pneumothorax during a lung biopsy.

BACKGROUND

Lung cancer is currently the leading cause of cancer death among both men and women. Accounting for 155,000 deaths per year in the U.S, this number is expected to rise especially in third world countries due to high pollution levels and high rates of smoking.

Anatomy of Pulmonary System (FIG. 1)

The lungs which sit on opposite sides of the heart can be distinguished by the number of lobes. The right lung is divided into three lobes while the left lung has two lobes. The lines which divide each lobe are known as fissures and are oriented at off angles to one-another causing the lobes to overlap each other.

Air is inhaled through the trachea and splits into the right and left lung at the bifurcation, better known as the carina. These smaller air pathways are bronchi which then evolve into secondary and tertiary bronchi, defined by smaller and smaller passageways. Towards the end of the air passageway the structure is referred to as a bronchiole which transports air to the final structure called the alveolar duct which comprises millions of alveoli facilitating gas exchange with the pulmonary vasculature.

The thoracic cavity, which houses the lungs, is delineated by the ribs ventrally, dorsally, and laterally. Between the ribs are intercostal muscles, which have fibers oriented in several different planes to aid in breathing. The external intercostal muscles aid in forced inhalation, as they help bend the ribs open to expand the transverse dimensions of the thoracic cavity. The internal intercostal muscles are responsible for the depression of the ribs, bending them inward thus decreasing the transverse dimensions of the thoracic cavity, aiding forced exhalation.

The lungs are enveloped in a thin serous membrane that dips into the fissures between the lobes, called the visceral pleura. This contiguous membrane is then reflected onto the outer aspect of the thoracic cavity (the innermost portion of the chest wall), called the parietal pleura, which is thicker than the visceral pleura. The space between the parietal and visceral pleura is called the pleural space, and is a potential space under normal physiologic conditions. The pleural space contains a serous fluid which aids the two layers in cushioning and sliding relative to one another. Additionally, the pleural space is a negative pressure space. Contraction of the diaphragm increases the volume of the thoracic cavity, thus creates a negative pressure within the pleural space causing the lungs to expand resulting in passive exhalation and active inhalation.

Solitary Pulmonary Nodule Biopsy Methods

There are several methods to determine if lung cancer is present. These include serial imaging, sputum cytology, or tissue sample (biopsy). Biopsies can occur in several ways such as bronchoscopy, mediastinoscopy, and image guided biopsy.

Bronchoscopy is a procedure which allows a doctor to look at your airways through a thin instrument called a bronchoscope. The bronchoscope comprises either a flexible or rigid tube which has a visualization element on the end such as a fiber optic camera. The most common type of bronchoscope used for diagnosing lung lesions is an Endobronchial Ultrasound (EBUS). This device comprises a small balloon with an ultrasound element and biopsy needle at the tip. Via the ultrasound, the doctor can locate the lung lesion and retrieve a sample using the needle. Some problems with EBUS include poor diagnostic yield from the needle and an inability to sample peripheral lesions due to size constraints of the device and bronchi.

Mediastinoscopy is a procedure to look at the mediastinum, the area between and in front of the lungs. During this procedure a small incision is made in the sternal notch or on the left side of the chest next to the sternum. A small scope is inserted allowing tissue biopsy to be collected via the scope. The rate of this procedure has decreased rapidly due to the rise of EBUS and image guided biopsies such as computed tomography (CT).

During CT-guided biopsy the physician is able to direct the percutaneous biopsy device using constant imaging. The biopsy retrieved during this procedure can be either a fine needle or core biopsy, core being favored by pathologists over the fine-needle biopsies retrieved during EBUS. This is because it's easier to determine malignancy because the tissue architecture is maintained and the sample is larger. The number one complication during CT-guided lung biopsy is a pneumothorax which occurs 25-35% of the time. Furthermore, 5-15% of all CT-guided lung biopsy cases result in further observation or hospitalization due to pneumothorax. The definitive treatment for a pneumothorax is a chest tube to help re-expand the lung. This causes pain for the patient and increased costs for the healthcare system.

A pneumothorax, also called a collapsed lung, is defined as the entry of air into the pleural space. During a CT-guided biopsy a tract is made both through the chest wall and the lung parenchyma leading to the suspected lesion. Due to the inherent negative pressure of the pleural space, air from both outside the body and inside the lung will try and create equilibrium by filling the pleural space. When too much air enters this space an outside pressure is placed on the lung causing it to collapse. To diagnose a pneumothorax a physician will perform a CT-scan or X-Ray immediately after the biopsy, 2 hours after the biopsy, and 4 hours after the biopsy. If the physician believes the patient is not at risk of a pneumothorax after imaging, the patient is sent home.

Although the physician cannot definitively determine which patients will develop a pneumothorax from a biopsy, there is a general consensus about which patient population and lesion type have increased risk of pneumothorax. For example, patients with emphysema are at higher risk of a pneumothorax. Emphysema causes the alveoli within the lungs to become damaged eventually weakening and rupturing. This causes larger air spaces and reduces the overall surface area of the lung thereby reducing the amount of oxygen that reaches the blood stream. When exhaling, the damaged alveoli don't exchange oxygen properly and air becomes trapped leaving no room for fresh oxygen-rich air to enter. The outer periphery of the lung can become so weak and trapped with air that a bullae can form. The trapped air in the periphery of the lungs and bullae acts as a source of air when crossed with a biopsy device and therefore contributes to the higher rate of pneumothorax in emphysematous patients.

Other factors which contribute to higher rates of pneumothorax are needle angle, needle path length, and transfissure lesions. During the procedure the physician will try and maintain a perpendicular path relative to the bronchial tree which minimizes the amount of the bronchiole that is crossed by the biopsy device. Additionally, the physician will try and take the shortest path possible without crossing fissures. As discussed previously, the right lung has three fissures defining the lobes while the left lung has two. Because each lobe is covered by a discrete visceral pleura layer avoiding a fissure is a necessary precaution. Rates of pneumothorax are higher as more pleural surfaces are crossed because it is creating more sources of entry for air.

Current Techniques for Preventing Pneumothorax

The techniques currently employed either involve plugging the biopsy tract or attempting to remove excess air. For example, some physicians attempt to use a saline or blood patch. In this method saline or blood is injected post-biopsy into the needle tract. These fluids act as a barrier to air entering into the pleural space. Another technique is called air aspiration which uses a syringe to suck air from the pleural space post-biopsy relying on the internal physiological healing mechanisms to seal the tract.

There is currently one FDA approved device on the market with an indication to prevent pneumothorax during computed tomography (CT)-guided lung biopsy. The device which is commercialized under the name BioSentry™ utilizes a desiccated PEG-hydrogel plug which is inserted post-procedurally. The plug is hydrated from both fluids inside the lung tissue and a saline drop applicator. The plug has a limited volumetric expansion and limited length. In addition, many pneumothoraces occur upon immediate entry into the pleural space and entry into the lung parenchyma with the biopsy device. Therefore, there is a need for a device to prevent air from entering the pleural space immediately upon entry of the biopsy device into the pleural space (e.g., across one or more pleural membranes) and lung parenchyma, preferably while not interrupting the tissue collection process and being configured to be compatible with standard biopsy tools.

SUMMARY OF THE DISCLOSURE

In view of the foregoing, it would be desirable to provide an apparatus and method to prevent pneumothorax by providing a seal against air upon percutaneous entry into the intercostal muscles, pleural space, and lung tissue. Desired outcomes of the apparatus and methods include reduced rates of pneumothorax and hospitalizations due to chest tube placement as well as higher patient satisfaction.

Disclosed herein are devices configured to reduce pneumothorax during CT-guided lung biopsy, specifically a device that will prevent all sources of air, including but not limited to air external to the patient and internal air from the lungs without adding time to the procedure. A proposed method of preventing pneumothorax comprises deploying a biomaterial (in preferred embodiments a sealant such as a biosealant) along the entire track length upon immediate entry into the tissue. Additionally, the proposed device has the ability to span fissures, the dividing areas between the lobules of the lung.

In one embodiment, this disclosure provides a delivery sheath including: an elongated body extending distally from the handles defining an inner lumen, the elongated body comprising a longitudinal folding line, the inner lumen housing a sealant, the distal end of the elongated body comprising an atraumatic tip. The delivery sheath may be configured to extend through the intercostal muscles, pleural space, and lung tissue thereby positioning the sealant along the entire track length. It is envisioned that the sealant can be slidably housed within the delivery sheath. Additionally, the sealant can take a cylindrical form to allow for positioning over the trocar. Further, the sealant can be delivered to the target lesion before removal occurs or during removal of the device. Additionally, multiple sealants can be delivered at different orientations or to the same tract. The multiple sealants can be inserted through different access sites and can overlap or be discrete from one another. The multiple sealants can have the same or different material properties. For example, if multiple sealants are delivered they may have different viscosities, crosslinking times, or stimuli such as pH, fluid, blood, saline, temperature, light, electron-beam, gamma-radiation, UV, DNA, enzymes, and other suitable initiators.

The delivery sheath may contain multiple compartments to house multiple sealants or a sealant and cross-linking material or a sealant and stimulus from the list above. The compartments may be oriented horizontally or longitudinally or in any desired shape to control the activation time and material properties of the sealant when delivered.

A variety of sealants may be delivered to the tissue, in some embodiments the sealant can comprise materials from the group consisting of collagen, hydrogels, polylactic acid, hyaluronic acid, polyethylene glycol and other suitable hydrophilic agents. The sealants and cross-linkers can be in solid-form, desiccated, powder form, liquid form, or a combination of the forms listed. The sealant must be able to adhere to the tissue and withstand the pressure of the lung during both inhalation and exhalation.

The novel delivery solution is not limited to only the lung. For example, it may provide a means to seal an incision to an artery thereby performing hemostasis. Due to the cylindrical nature of the device it is capable of being threaded onto a guidewire. The delivery sheath housing the sealant can be advanced to the artery, the sheath can then be removed leaving the sealant in place, the sealant can cross-link in reaction to a predetermined stimulus such as blood, natural fluid within the tissue, saline, temperature, light, electron-beam, gamma-radiation, UV, DNA, enzymes, and other suitable stimuli.

Another embodiment is directed towards constant insertion of a sealant throughout the procedure. This embodiment comprises an elongated body comprising a distal tip, the tip being configured to puncture tissue, the elongated body also comprising a side port towards to distal end which provides access to an internal lumen which is in fluid communication with a proximal end reservoir, the proximal end reservoir containing a sealant and a means of injecting the fluid through the internal lumen and out the side port. This embodiment allows the user to deposit biosealant within the chest wall, pleural space, visceral pleural, parietal pleura, lung parenchyma, or target site within the lung intraoperatively.

Another aspect of the invention is directed towards a kit directed towards sealing a tissue tract within a subject. The kit comprises a housing, tissue introducer sheath, biomaterial reservoir, container for holding the components, and instructions for assembling and using the components.

Another aspect of the invention is directed towards a method of using the device. Upon insertion of the device into the subject biomaterial is delivered through the tissue introducer sheath to the tissue. The tissue includes but is not limited to chest wall, pleural space, visceral pleural, parietal pleura, lung parenchyma, lung fissures, and target sites within the lung. The biomaterial can be delivered as the device is inserted into the tissue or at anytime thereafter and can be used to prevent pneumothorax.

Another aspect of the invention is directed towards a device to prevent pneumothorax in a subject. The device comprises a hollow first needle with a sealed distal tip in fluid communication with a biomaterial reservoir. A second needle comprising an internal lumen and a septa located within the proximal end. Wherein the first needle is inserted through the hollow lumen of the second needle and is coupled via a coupling mechanism. Upon insertion of the device into the tissue, biomaterial can be continuously deployed through a distal port of the first needle to tissue including but not limited to chest wall, pleural space, visceral pleural, parietal pleura, lung parenchyma, lung fissures, and target sites within the lung. The device can be located within a kit comprising a container, instructions for assembling and using the components.

In some embodiments, this disclosure provides a device configured to deposit a biomaterial in a subject, wherein the device comprises: a housing comprising a housing exterior, a housing lumen, a housing proximal end, and a housing distal end; an introducer comprising an introducer lumen, an introducer proximal end, and an introducer distal end; the introducer being positioned within the housing lumen; a delivery sheath comprising delivery sheath tabs and at least one folding line, and being positioned around the housing exterior; and, one or more biomaterials between the delivery sheath and the housing exterior Kits as well as well as methods of making and using the same are also provided comprising the same are also provided.

In some embodiments, this disclosure provides a device for depositing biomaterial, optionally a sealant such as a biosealant, within a tissue, the device comprising: a housing comprising a housing proximal end, a housing lumen, a housing sheath, and a housing distal end; and, a tissue introducer positioned within the housing lumen and comprising a tissue introducer lumen, a tissue introducer proximal end, and a tissue introducer distal end comprising a port located on the side wall of tissue introducer. Kits as well as well as methods of making and using the same are also provided comprising the same are also provided.

In some embodiments, this disclosure provides a device for depositing biomaterial, optionally a sealant such as a biosealant, within a tissue, the device comprising: a housing comprising a housing proximal end, a housing lumen, a housing sheath, and a housing distal end; and, a tissue introducer positioned within the housing lumen and comprising a tissue introducer lumen, a tissue introducer proximal end, and a tissue introducer distal end comprising a port located on the side wall of tissue introducer. Kits as well as well as methods of making and using the same are also provided comprising the same are also provided.

In some embodiments, this disclosure provides a sealant delivery device assembly comprising: a) a housing sheath component comprising a housing proximal end comprising a housing opening, a housing sheath surrounding a housing lumen, and a housing distal end; and, b) a tissue introducer component comprising a tissue introducer lumen, a tissue introducer proximal end, an articulable hub, one or more ports, and a tissue introducer distal end; wherein said the tissue introducer component is positioned within the housing sheath component, the tissue introducer lumen being surrounded by housing sheath wherein at least one of said one or more ports and the tissue introducer distal end protrude from the housing distal end. In some embodiments, this disclosure provides a kit comprising: a) a housing component comprising a housing proximal end, a housing lumen, a housing sheath, and a housing distal end; and, b) a tissue introducer component comprising a tissue introducer lumen, a tissue introducer proximal end, and a tissue introducer distal end comprising a port positioned on the side wall of the tissue introducer distal end. Methods of making and using the same are also provided.

In some embodiments, this disclosure provides a device configured for applying a biomaterial to a tissue, the device comprising: a) a first needle comprising: a first needle closed distal tip, a first needle proximal articulation hub comprising a first needle proximal articulation hub coupling mechanism on its distal end, a first needle distal port located proximally to the first needle sealed distal tip, and a first needle hollow lumen in fluid communication with the first needle port and a biomaterial reservoir; and, b) a second needle comprising: a second needle internal lumen, a second needle proximal housing comprising: a second needle septa configured to allow passage of the first needle into the second needle internal lumen without a pressure change from the proximal side to distal side of the membrane, and a second needle proximal housing coupling mechanism located on the proximal end of the second needle; and, a second needle open distal end; wherein, when the first needle proximal articulation hub coupling mechanism is coupled to the second needle proximal housing coupling mechanism, the first needle is positioned within the second needle internal lumen and the first needle distal port is distal to the second needle open distal end Methods of making and using the same are also provided. Kits as well as well as methods of making and using the same are also provided comprising the same are also provided.

In some embodiments, this disclosure provides a device for depositing biomaterial within a tissue, the device comprising: a housing comprising a housing proximal end, a housing lumen, a housing sheath, and a housing distal end; and, a tissue introducer positioned within the housing lumen and comprising a tissue introducer lumen, a tissue introducer proximal end, a tissue introducer distal end, and at least one port. Kits as well as well as methods of making and using the same are also provided comprising the same are also provided.

In some embodiments of the methods disclosed herein, the biomaterial can be delivered to the tissue through the first needle hollow lumen, optionally wherein the device is inserted into tissue prior to delivering the biomaterial to the tissue, and/or the biomaterial is delivered to the tissue as the device is being inserted into tissue, and/or the biomaterial is delivered to the tissue as the device is being inserted into the tissue and as the device is being removed from the tissue. In some embodiments, this disclosure provides methods including: a) inserting into and advancing a device or a sealant delivery assembly as disclosed herein through a tissue, thereby forming a tissue tract; and, b) continuously depositing biomaterial from the port into the tissue tract as the device is inserted into and advanced through the tissue, and optionally as the device is removed from the tissue; and/or prior to step a), performing steps a1) of locating a target site in a tissue; and, a2) verifying that the device is on a correct trajectory to the target site, wherein: 1) if the device is not on a correct trajectory to the target site, retracting the device from the device tract while continuously depositing biomaterial into the device tract, and repeating step a1) and a2) until the device is determined to be on a correct trajectory to the target site; or, 2) if the device is on a correct trajectory to the target site following steps a1) and a2), advancing the device toward the target site while continuously depositing biomaterial into the device tract; and/or, d) removing the tissue introducer sheath from the housing lumen, or removing the first needle from the internal lumen of the second needle; e) inserting a biopsy tool into the housing lumen or internal lumen of the second needle and removing a biopsy sample from the tissue; f) verifying the biopsy sample is adequate; g) removing the biopsy tool from the internal lumen of the second needle; h) inserting the tissue introducer into the housing lumen or inserting the first needle into the internal lumen of the second needle, and continuously depositing biomaterial into the device tract as the tissue introducer or first needle is inserted into and advanced through the housing lumen or internal lumen of the second needle, respectively; and/or, i) performing post-procedure imaging to check for complications. In some embodiments, this disclosure provides methods for applying a biomaterial, optionally a biosealant, to a tissue using a biosealant delivery assembly comprising: a) a housing component comprising a housing proximal end, a housing lumen, a housing sheath, and a housing distal end; and, b) a tissue introducer component comprising a tissue introducer lumen, a tissue introducer proximal end, a tissue introducer distal end, and a port; wherein the biomaterial is deposited onto the tissue through the port.

In some embodiments, this disclosure provides methods for making a sealant delivery device assembly or a component thereof by: producing a housing sheath component comprising a housing proximal end comprising a housing opening, a housing sheath surrounding a housing lumen, and a housing distal end; producing a tissue introducer component comprising a tissue introducer lumen, a tissue introducer proximal end, an articulable hub, one or more ports, and a tissue introducer distal end; and, to produce the sealant delivery device assembly reversibly connecting the housing sheath component and the tissue introducer component, wherein said the tissue introducer component is positioned within the housing sheath component such that the tissue introducer lumen being surrounded by housing sheath wherein at least one of said one or more ports and the tissue introducer distal end protrude from the housing distal end.

Additional aspects and embodiments are described and/or claimed herein.

DETAILED DESCRIPTION

As used herein, the singular forms "a", "an", and "the" refer to one or more than one, unless the context clearly dictates otherwise.

An important aspect of the present invention is the ability to deploy a sealant immediately upon introducing the device into tissue. The present invention reduces the risk of complications associated with accessing the lung parenchyma. The devices and methods are used with sealant compounds which have a suitable density, viscosity, modulus and other material properties to effectively seal the tract to prevent the passage of liquid or gas. Thus, in some embodiments, this disclosure provides a device that can be used to deposit or deploy (e.g., continuously) a biosealant into a needle tract as a needle is being inserted into a tissue and as the needle is being removed from the tissue, such that air and/or fluids cannot enter the needle tract during or after insertion and/or removal of the needle from the tissue is/are completed.

Figure 1:
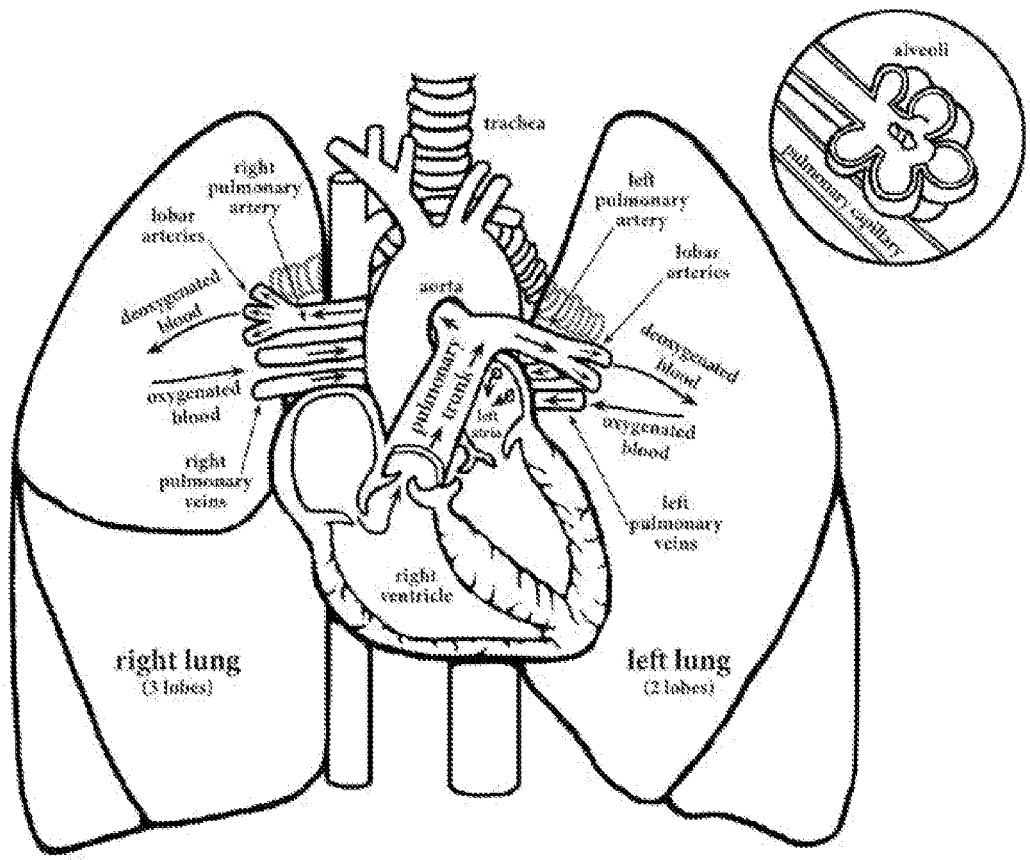
FIG. 1 illustrates the anatomy of the pulmonary system.
Figure 2:
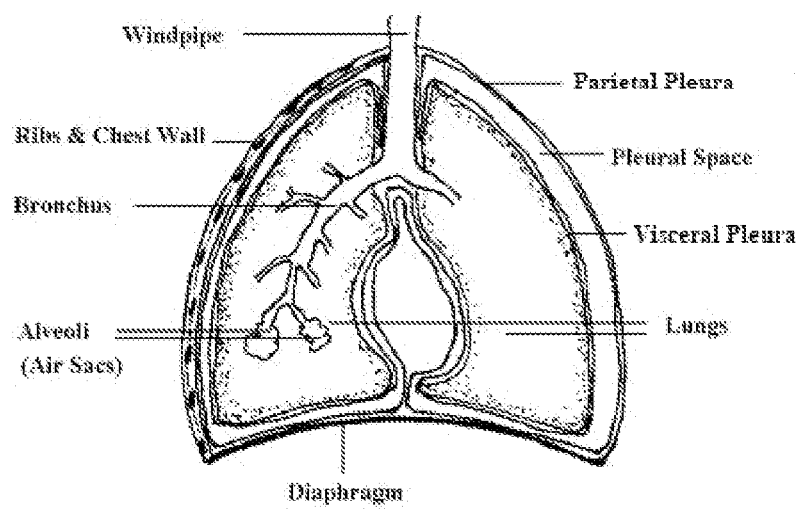
FIG. 2 illustrates the anatomy of the pulmonary system specifically the pleural space.

The respiratory system is illustrated in FIG. 1. More specifically the trachea 45 splits at the carina 46 and leads into left lung 48 and right lung 50. The airways, also termed bronchi and bronchioles 52 become smaller as they travel towards the periphery of the lung and eventually end in alveoli 54 which aid in gas exchange. As shown in FIG. 2 The pleural cavity 60 is located between the visceral pleura 58 and the parietal pleura 59. The pleural space is a negative pressure area which helps the lungs expand and keeps them inflated within the thoracic cavity which is defined by the ribs and chest wall 57. Both the visceral and parietal pleura are coated with a serous fluid which acts as a lubricant to help them slide and cushion relative to one another during the respiration process. When the pleural space is compromised the lungs can no longer retain their suspended status within the thoracic cavity and they decompress making the respiration process harder on the individual. In most cases, if fluid or gas enters the pleural space an intervention must occur such as a chest tube or surgery.

Figure 11:
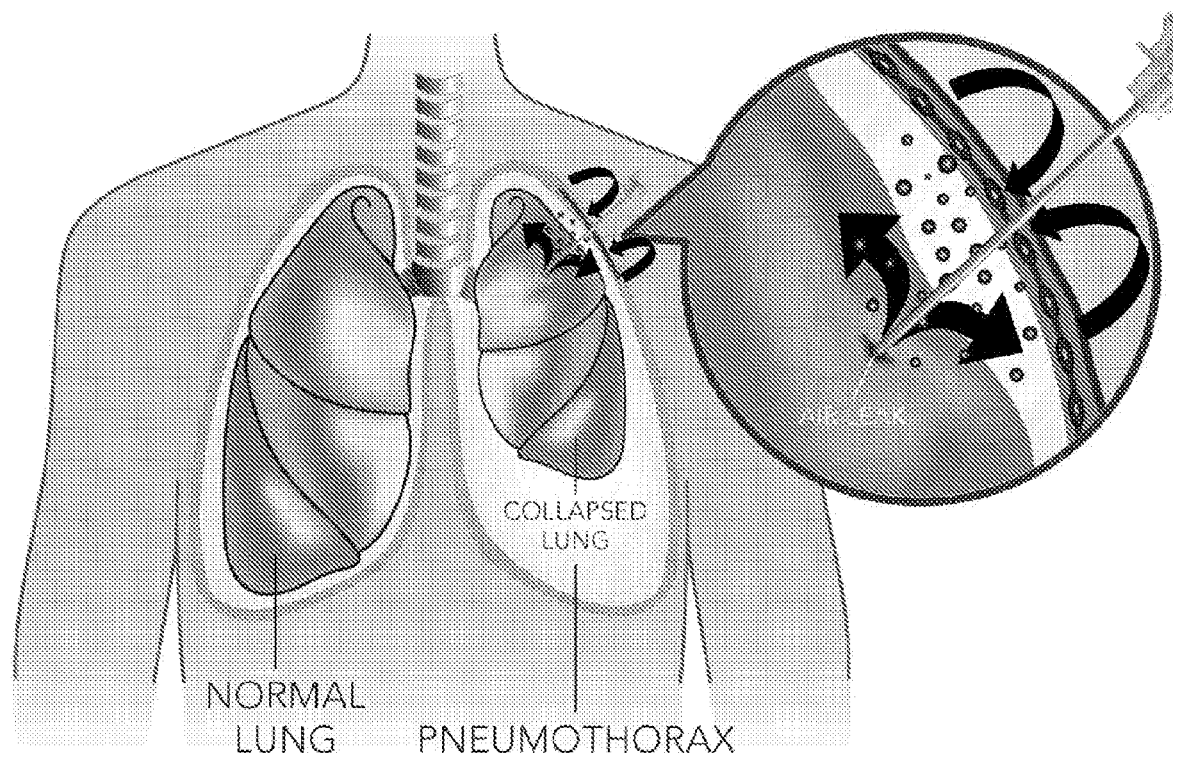
FIG. 11 illustrates the potential air entry method into the pleural space.

The pleural space is most commonly compromised when trauma occurs to the chest wall causing a passageway to form from the skin through the lung parenchyma. Lung parenchyma is understood by those of ordinary skill in the art to include those portions of the lung that perform the gas exchange function of the lung, including but not limited to alveoli. This usually results in a spontaneous tension pneumothorax which can place a large outside force on the heart. Iatrogenic pneumothoraces result from transthoracic needle aspiration procedures, EBUS procedures, pleural biopsies, thoracentesis, tracheostomy, and cardiopulmonary resuscitation. The pleural space can also be filled with fluid such as blood (also referred to as a hemothorax) resulting from blunt trauma, penetrating trauma such as the biopsy methods listed above, nontraumatic or spontaneous neoplasia (primary or metastatic), complications from pulmonary embolisms, torn pleural adhesions, bullous emphysema, tuberculosis, arteriovenous fistulae, thoracic aortic aneurysm, intralobar and extralobar sequestration. For example, FIG. 11 depicts the lungs wherein a biopsy device compromises the pleura and enters into the lung parenchyma. Due to the high-density structure of the bronchial tree the biopsy device will cross many airways and alveoli 54 providing air to enter the pleural space and possible induce a pneumothorax as indicated by the internal arrows. Additionally, air may also enter from the external environment as indicated by the external arrows.

As will be appreciated by persons skilled in the art, the invention and its embodiments have been described with respect to procedures involving lung tissue, However, certain aspects of the device and method such as the sealing device and component are applicable to other procedures and devices suitable for use elsewhere in the body. These may include but are not limited to kidney, liver, connective tissue, breast, pancreas, spleen, brain, joints, bladder, prostate, mediastinum, muscle, and gastrointestinal tract. Treatment modalities include but are not limited to filling voids in tissue, repairing needle tracts, and repairing wounds or deformations.

Throughout the embodiments described herein, multiple terms may be used to the same part. For example, the introducer or tissue introducer 18 can be called a first needle; the housing 19 can be called a second needle; delivery sheath proximal end can be called a proximal articular hub; septa can be called a fluid-static membrane.

As used herein, the term "coupled" generally means physically coupled or linked and does not exclude the presence of intermediate elements between the coupled items absent specific contrary language.

As used herein, the term "subject" can include a living human subject, cadaver, swine model, canine model, rabbit model, mouse model, or rat model.

As used herein, the term "tissue" can include any tissue within the body. The present invention focuses on the chest wall, pleural space, parietal pleura, visceral pleura, lung parenchyma, bronchioles, alveoli, airways, lung lesions, and lung fissures. However, the device can also relate to different organs including but not limited to kidney, liver, connective tissue, breast, pancreas, spleen, brain, joints, bladder, prostate, mediastinum, muscle, and gastrointestinal tract.

As used herein the term biomaterial reservoir can include a syringe including a piston which is manually compressed to extrude a fluid or sealant. It may include a deformable reservoir which is manually compressed to extrude a fluid or sealant.

The materials (i.e., typically a sealant (e.g., biosealant)) used to prevent the passage of liquid or gasses (e.g. to seal) can include hydrogels, polymers, human biologic materials, gels, glues, adhesives. Numerous sealants would be optimal for use with various embodiments, including those composed of synthetic or natural hydrogels that swell in the presence of biological fluids, polymers including stimuli-responsive polymers, proteins, crosslinkers, and buffers such as phosphate, carbonate, bicarbonate, borate, imidazole, or other mixtures, initiators, and stabilizers to stabilize the components. The stimuli can include but are not limited to pH, fluid, blood, saline, temperature, light, electron-beam, gamma-radiation, UV, DNA, enzymes, and other suitable initiators. The viscosity of the sealant should be greater than water and be conducive to proper deployment from the device. The sealant may go through a liquid or gel to solid transition after deployment into the needle tract. Set time should occur shortly after implantation into the body, preferably within 1-60 seconds. However, it may be preferable to have a longer transition time for example 1-5 minutes, or 5-10, minutes or 10-15 minutes, or 15-20 minutes, or greater than 20 minutes. The sealant may also be hemostatic, aiding in the clotting cascade. Hemostatic materials may also be added to the sealant, including but not limited to chitin derivatives such as carboxymethyl chitin and chitosan. The sealant may also act as a glue, causing the tissue walls to seal against one another.

Preferably, the sealant is biocompatible, biodegradable, will not cause a foreign body response or inflammation, be uniformly delivered to the needle tract, and have similar properties of intrinsic lung tissue. These properties include elasticity, modulus, stiffness, brittleness, strain, cohesion, adhesion, and stress. It is desirable for the sealant to have properties similar to that of the surrounding tissue to prevent patient irritation after the procedure. For all embodiments, sealant properties such as mechanical properties, set time, cure time, viscosity, biocompatibility, degradation rate, and radiopacity can be tuned selectively. For example, increased cross-linking due to higher concentrations of the crosslinking agent, may increase stiffness and other mechanical properties. Fillers, plasticizers, and adhesion modifiers may also be added to further modify material properties. To induce a natural adhesive response, biochemical or chemical agents such as proteins or nucleic acids in the range of 100 nm to 1 mm can be added. Examples of these agents include bleomycin, cytokines, chemokines, and single-stranded RNA molecules. Set time can depend on the means of material delivery through the various embodiments. The formulation can also contain set time modifiers that can either increase set time, such as addition of glycerol, or decrease set time, such as addition of carboxymethyl cellulose. The addition of materials to change viscosity include biocompatible agents with viscosities greater than water, including glycerol, oils, lipids, fatty acids, proteins, carbohydrate-based polymers, and synthetic polymeric materials commonly used as pharmaceutical excipients. These components can vary in viscosity from 1 to 1000 centispokes. Radioactive labels may also be added to via mixing or chemical conjugation to change the sealant's radiopacity.

Additionally, the sealant may include radiographic and radiopaque particles including but not limited to radioisotopes, iodine and iodine compounds, metals such as gadolinium, gold, platinum, silver, or tantalum, barium sulfate powder, polymers, and/or a combination thereof.

Suitable sealants can include implantable hydrogels that may be synthetic, natural, or a combination thereof. Natural products include hyaluronic acid, chitins, chitosans, and alginates, as well as polypeptides and polysaccharides like starch and dextran. Proteins including albumins, collagens, and gelatins can be used as crosslinkers with various polymers to form a suitable gel with a viscosity greater than water. Protein crosslinkers for further processing of natural hydrogels include but are not limited to aldehydes such as gluteraldehyde, other polyaldehydes, and esters. Proteins can be derived from either natural, semi-synthetic, or synthetic processes. Synthetic hydrogels do not generally biodegrade and can be comprised of polymers such as poly (hydroxylalkyl methacrylates), polyacrylamide (PAM), polyvinylpyrrolidone (PVP), polyvinyl alcohol (PVA), polyglycolides including polyglycolic acid (PGA), polyactides including polylactic acid (PLA), polylactic-co-glycolic acid (PLGA), polycaprolactone (PCL), polydioxanone (PDO), poly(ε-caprolactone-co-glycolic acid) (PCGA), Poly (N-isopropylacrylamide) (PNiPAam), polyethylene glycol (PEG), polyethylene glycol diacrylate (PEGDA), polyethylene glycol dimethacrylate (PEGDMA), polyethylene oxide (PEO), polypropylene oxide (PPO), derivatives from triblock copolymers including to but not limited to PEO-PPO-PEO and PPO-PEO-PPO blocks, synthetic collagen, silicone, and synthetic gelatin. Furthermore, the sealant may in the form of a gel, liquid, or microsphere wherein the microsphere has a diameter in the range of 20-500 microns, or in the range of 1-100 nm. Biodegradability of the sealant composition can be increased by adding monomers from the groups including but not limited to glycolide, lactide, ε-caprolactone, p-Dioxanone, and Trimethylene Carbonateln. The hydrogels described above could be formulated to swell and expand in the presence of aqueous fluid (i.e. biological fluid from moisture of lung tissue), and be activated (i.e. change physical and chemical properties) upon exposure to pH, fluid, blood, saline, temperature, light, electron-beam, gamma-radiation, UV, DNA, enzymes, and other suitable initiators.

Additionally, or alternatively, the device of the present invention may be used to deliver a therapeutic substance such as antihistamines, analgesics, immunosupressive agents, coronary, cerebral or peripheral vasodilators, hormonal agents, antithrombotic agents, diuretics, antihypertensive agents, cardiovascular drugs, opioids or a combination of those thereof. Preferred therapeutic agents are those directed towards pulmonary diseases including but not limited to lung cancer and chronic obstructive pulmonary disorder. The amount of therapeutic agent to be delivered will be dependent on the disease state and can be varied over time.

In an alternative embodiment the sealant may comprise the form of sutures, clips, stents, or plugs. The stent, clips, or sutures can be formed from materially including but not limited to nitinol, stainless steel, PTFE, or a polymer or a combination thereof. The stent may include a graft covering on the inside or outside, the graft material being formed of silicone, PTFE, polyurethanes, polyethylenes, nylons, Dacron, Teflon or other elastic material to help seal the stent and prevent gas and fluid leakage. The sutures and clips can preferably comprise a shape-memory material in which the material transforms to a shape which seal the gas and fluid or causes the tract to deform thereby creating a seal.

Figure 3:
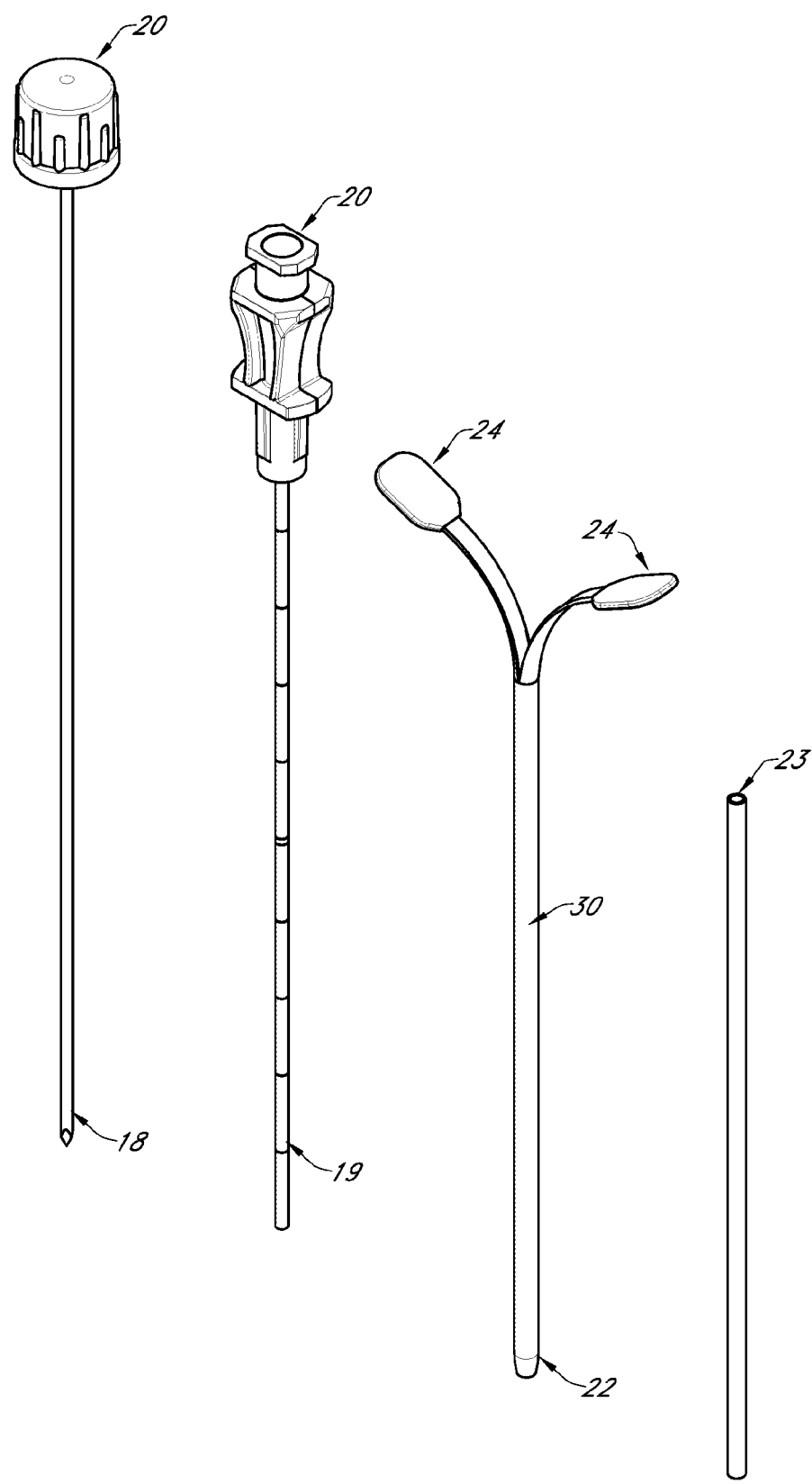
FIG. 3 illustrates a device adapted to deploy a sealant throughout the length of the tract immediately upon entry into tissue.

FIG. 3 illustrates a device adapted to deploy a sealant along the entire length of the needle tract. The device consists of an introducer 18 comprising a proximal end 20. The introducer fits within the housing 19 which also comprises a proximal end 21. The delivery sheath 22 houses the sealant 23 and is slidably connected on top of the housing 19. The delivery sheath 22 also comprises delivery sheath tabs 24 which are located on the proximal end and help with removal of the sheath. The delivery sheath 22 can be located at any length along the housing 19; for example, it may only be located distally, proximally, centrally, or the entire length of the housing 19. Furthermore, the delivery sheath 22 comprises a folding line 30 which has a smaller wall thickness allowing for easier separation of the delivery sheath 22 upon an applied force to the delivery sheath tabs 24. The delivery sheath 22 can contain multiple folding lines at different orientations relative to one another, for example folding lines 30 can be located 180 degrees from one another to allow for easy separation. In some embodiments, the folding line is a perforated line. In some embodiments, multiple folding lines, which can be perforated lines, may be present. In some embodiments, such multiple folding lines may be orientated approximately opposite one another to provide for ease in separating the delivery sheath (e.g., 22) from the device by applying a pulling forces on each of the delivery sheath tabs (e.g., 24).

The device of FIG. 3 is configured to enter the tissue as an integral unit. Once the device has been advanced to the desired location, the delivery sheath 22 is separated by pulling on the delivery sheath tabs 24. Subsequently, the sealant 23 is exposed to the tissue and can transform or immediately act as a barrier to prevent the flow of fluid or gas throughout the tract. Additionally, the sealant 23 can act as a barrier to the migration of cells. For example, if the device is advanced to a location containing cancer cells, the sealant 23 can block the cells from migrating throughout the tract.

The sealant 23 can be in any form such as solid, liquid, or gel. Additionally, the sealant may be different shapes including but not limited to cylinder, rod, or microspheres. The delivery sheath 22 may contain different compartments within to hold different sealants or cross-linking materials. For example, there may be longitudinally oriented compartments which each contain a different polymer or cross-linking material, upon removal of the delivery sheath 24 the materials will combine to act as a sealant.

Figure 4A:
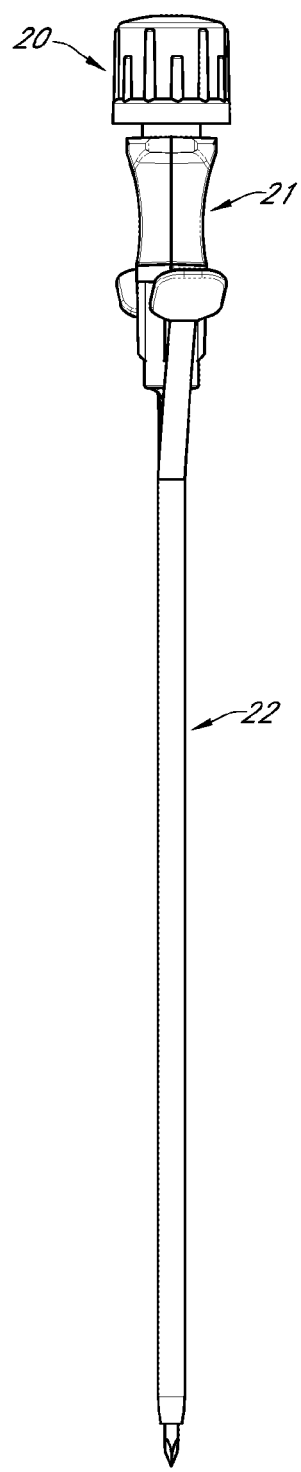
FIGS. 4A-4C illustrate a device adapted to conform with standard biopsy tools and a cross-sectional view of the device.
Figure 4B:
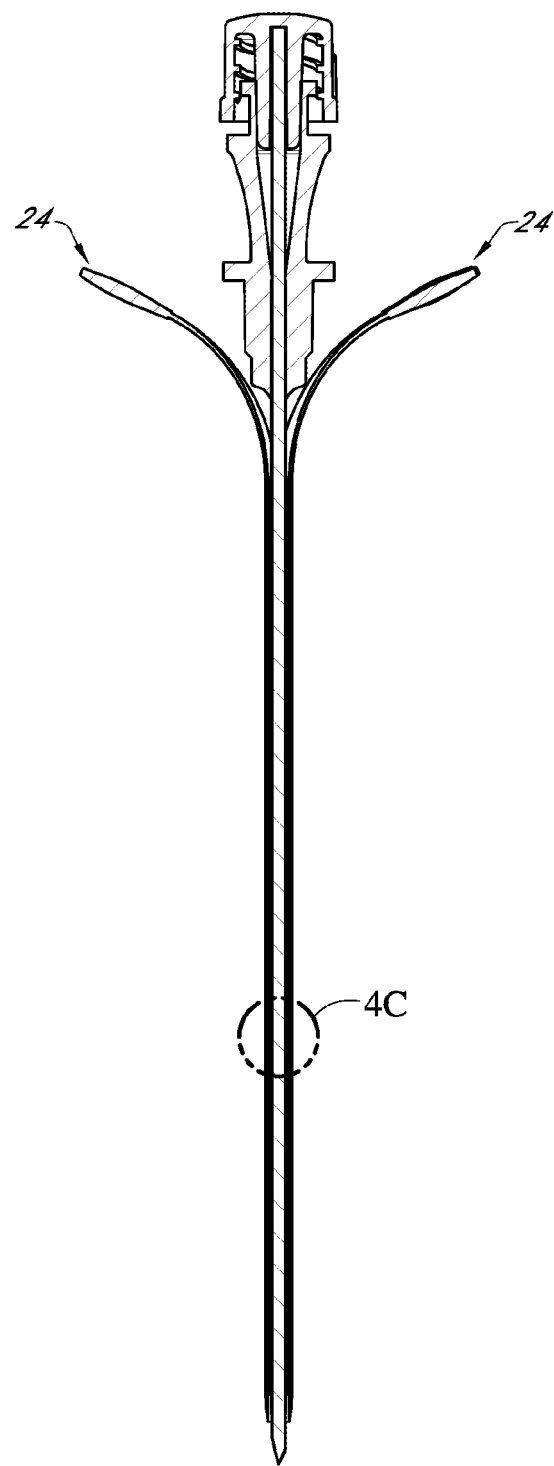
Figure 4C:
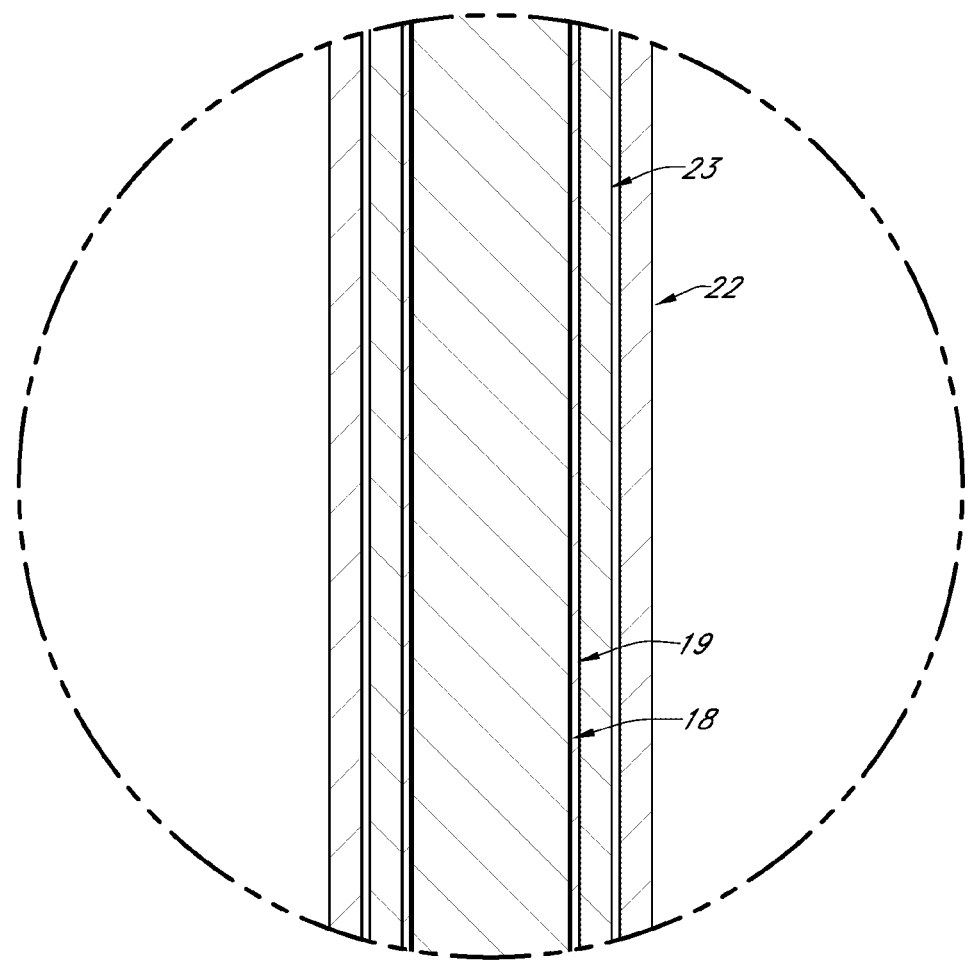

FIG. 4 illustrates the device of FIG. 3 as an integral unit. As stated previously, the delivery sheath 22 containing the sealant 23 is configured to slidably connect to the housing 19. The sealant 23 sits between the delivery sheath 22 and housing 19 and acts as a barrier to fluids and gasses once the delivery sheath 22 is removed and the sealant 23 is exposed to the in vivo environment. As stated previously, the sealant 23 can be a material that swells in reaction to a stimuli including but not limited to pH, fluid, blood, saline, temperature, light, electron-beam, gamma-radiation, UV, DNA, enzymes, and other suitable initiators. Additionally, the sealant 23 may react to another cross-linkable material which may be combined within the sheath 22 or added after the sheath 22 is removed.

Figure 5A:
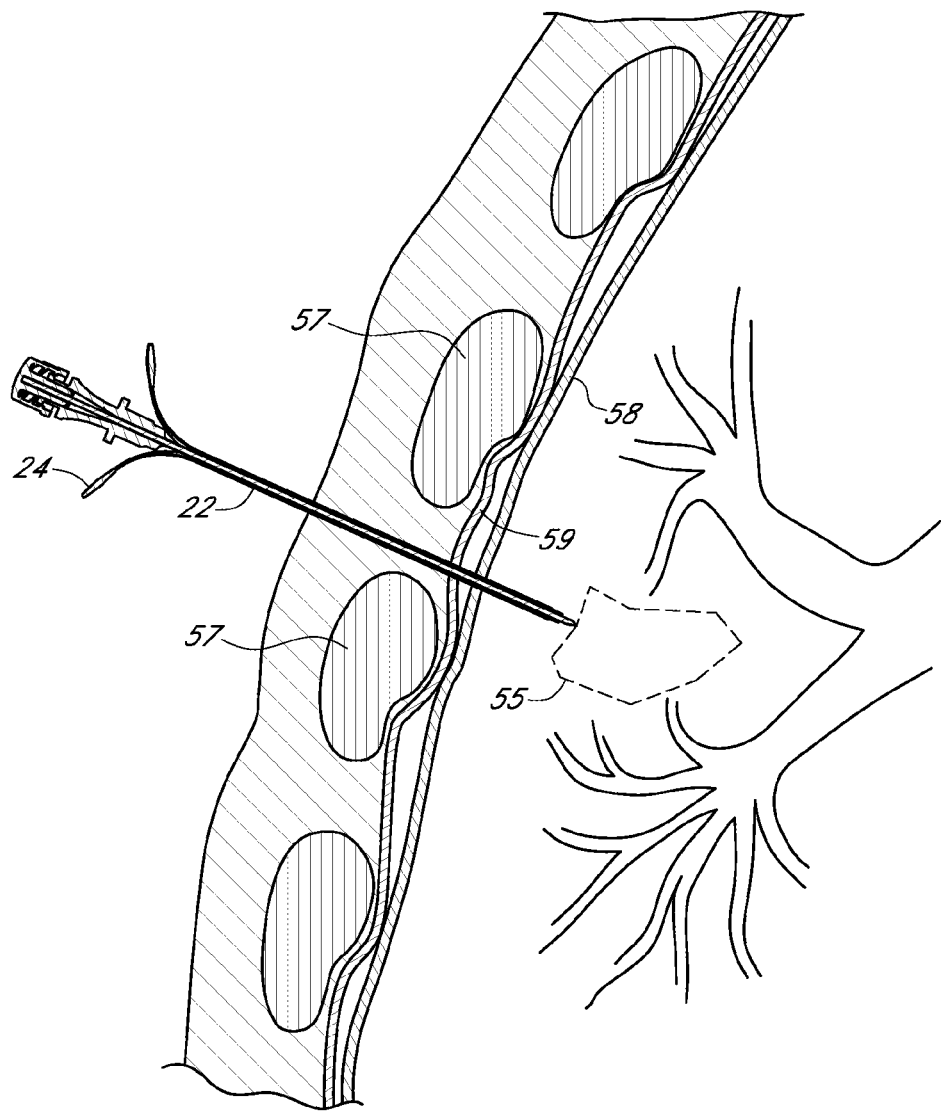
FIGS. 5A-5D illustrate the device of FIG. 4 as used in the procedure.
Figure 5B:
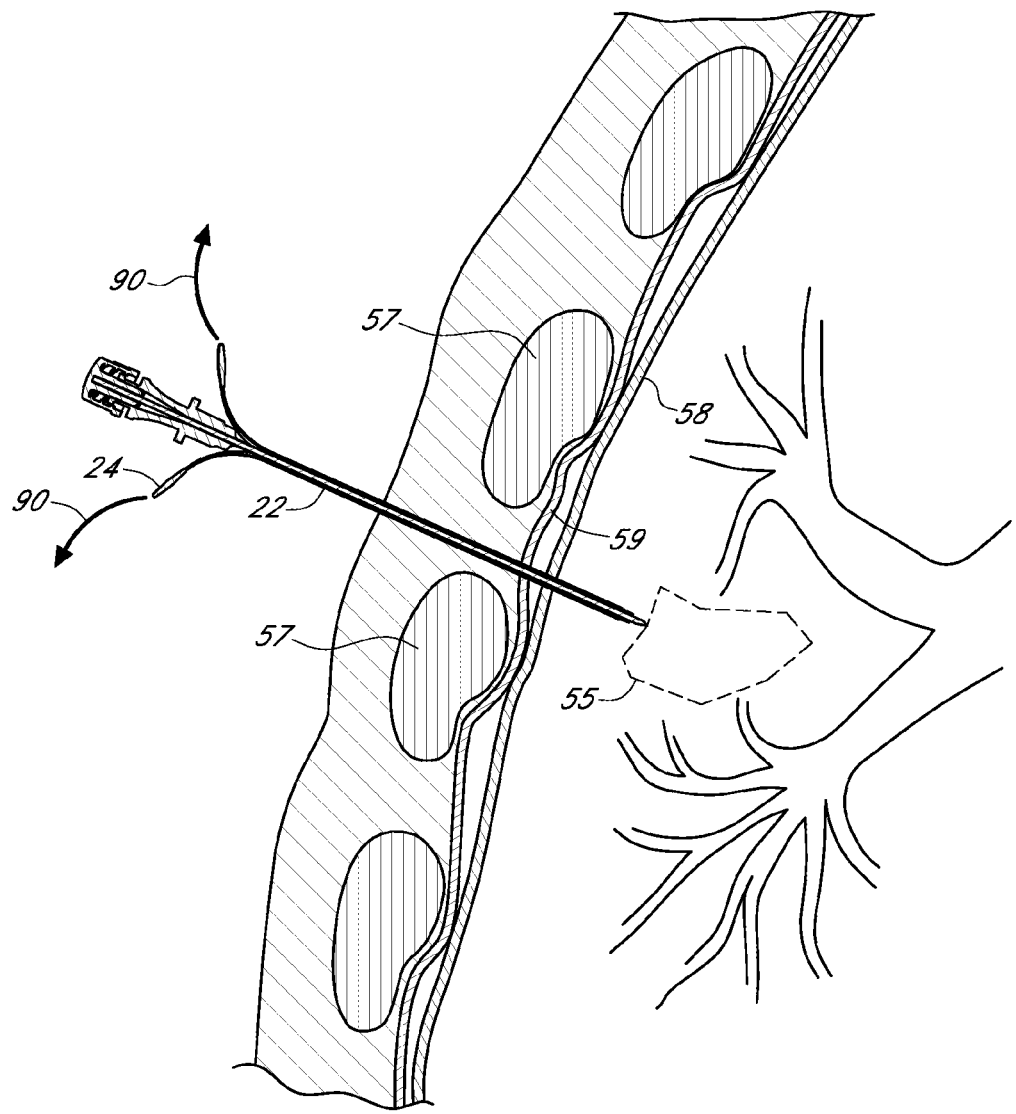

FIGS. 5A-5D illustrate the device of FIG. 4 as used in the procedure. Referring to FIG. 5A, the device is inserted as an integral unit until it abuts the lesion 55. The delivery sheath 22 houses the sealant 23 and crosses the pleural space 60 defined by the visceral pleura 58 and the parietal pleura 59. Referring to FIG. 5B, once the device is at the intended location the sheath is removed as indicated by the separation force lines 90. The removal of the sheath then exposes the sealant 23 to the in vivo environment. The sealant 23 will immediately act as a sealant blocking fluids and gases from traveling through the needle tract and ultimately the pleural space 60. The sealant can be tuned to swell or change material properties including but not limited to adhesiveness, viscosity, liquidity, density, hardness, or flexibility in reaction to certain stimuli including but not limited to pH, fluid, blood, saline, temperature, light, electron-beam, gamma-radiation, UV, DNA, enzymes, and other suitable initiators. Additionally, another cross-linking material may be added to increase or decrease the reaction time.

Figure 5C:
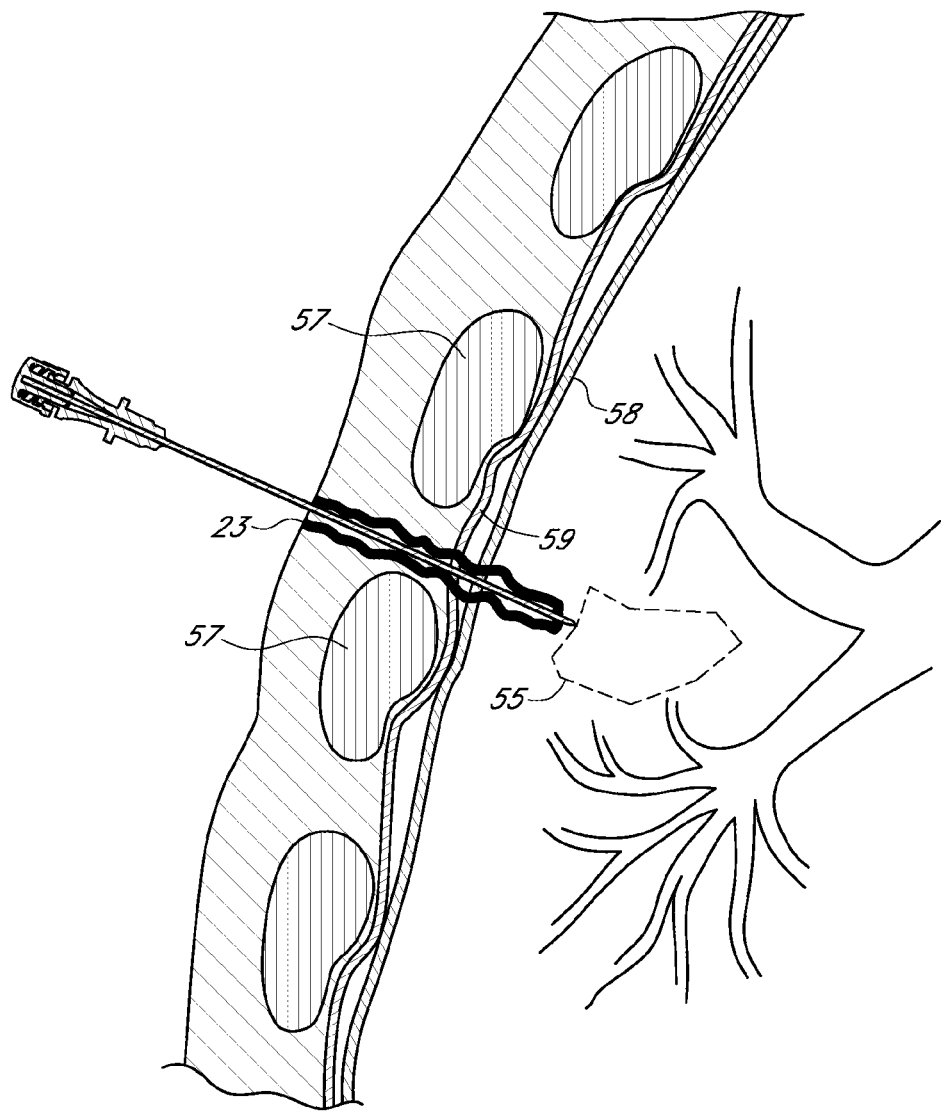
Figure 5D:
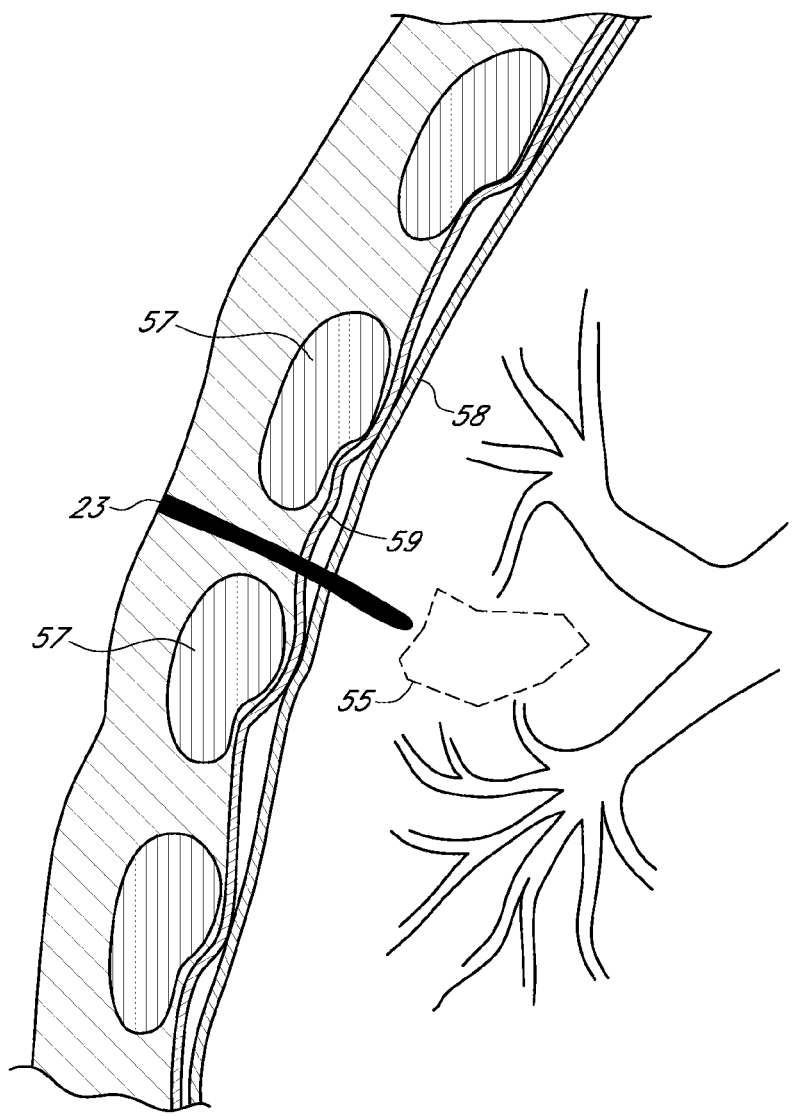

FIG. 5C illustrates how the present device can act as a seal within the needle tract during the procedure while allowing tissue collection to occur via the lumen of the housing 19. FIG. 5D illustrates that upon removal of the device, the needle tract is filled with the sealant 23 which prevents any fluid or gases from traveling through the tract which may induce complications including but not limited to a pneumothorax or hemothorax. Those skilled in the art will appreciate that the delivery sheath 22 is not limited to only large bore needle devices. The delivery sheath 22 can be adapted to fit any size and therefore provide an adequate seal along the entire length of the tissue tract. Furthermore, the material properties of the sealant 23 can be altered to provide a faster sealing affect or multiple sealants can be delivered at different times and locations with the present device.

Figure 6A:
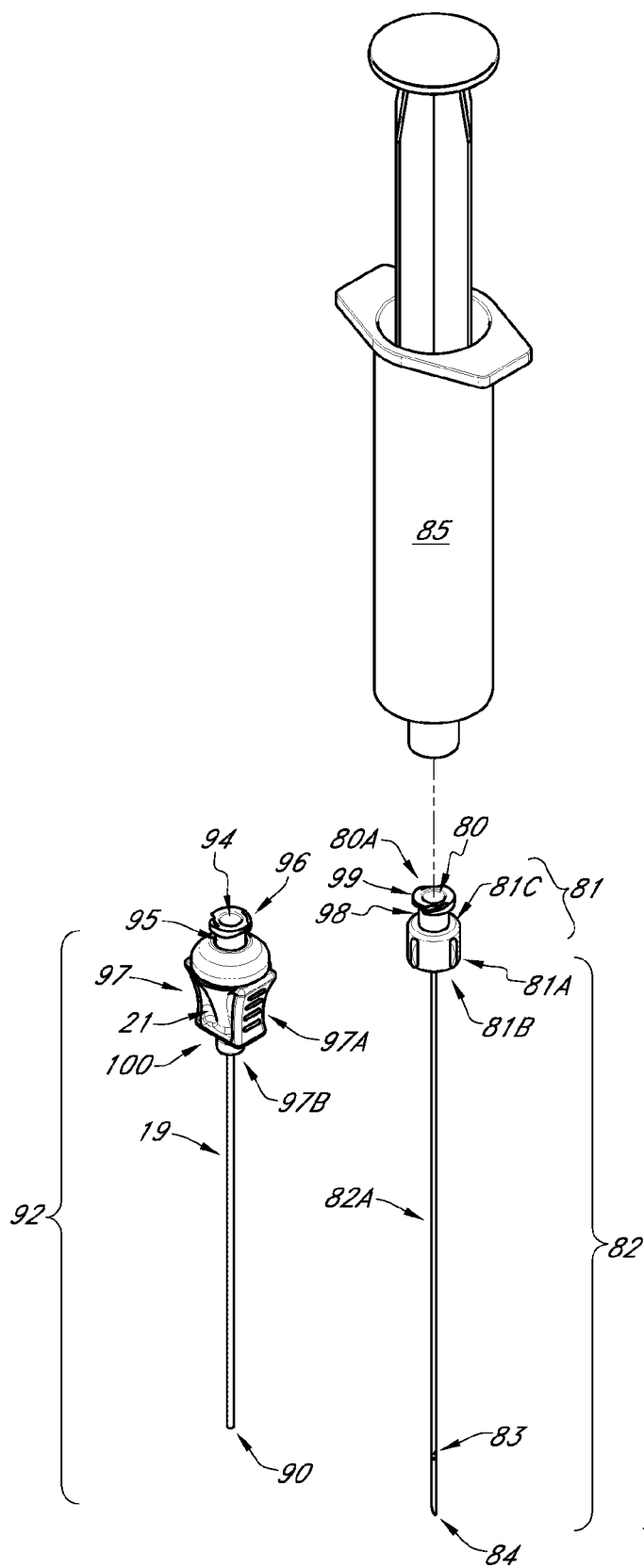
FIG. 6A-6G illustrate additional embodiments adapted to deploy a sealant throughout the length of the tract at any time during the procedure.
Figure 6B:
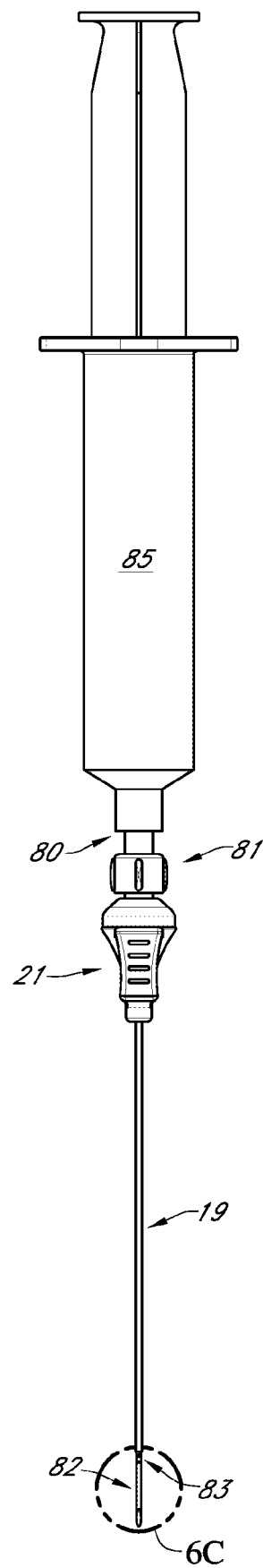
Figure 6C:
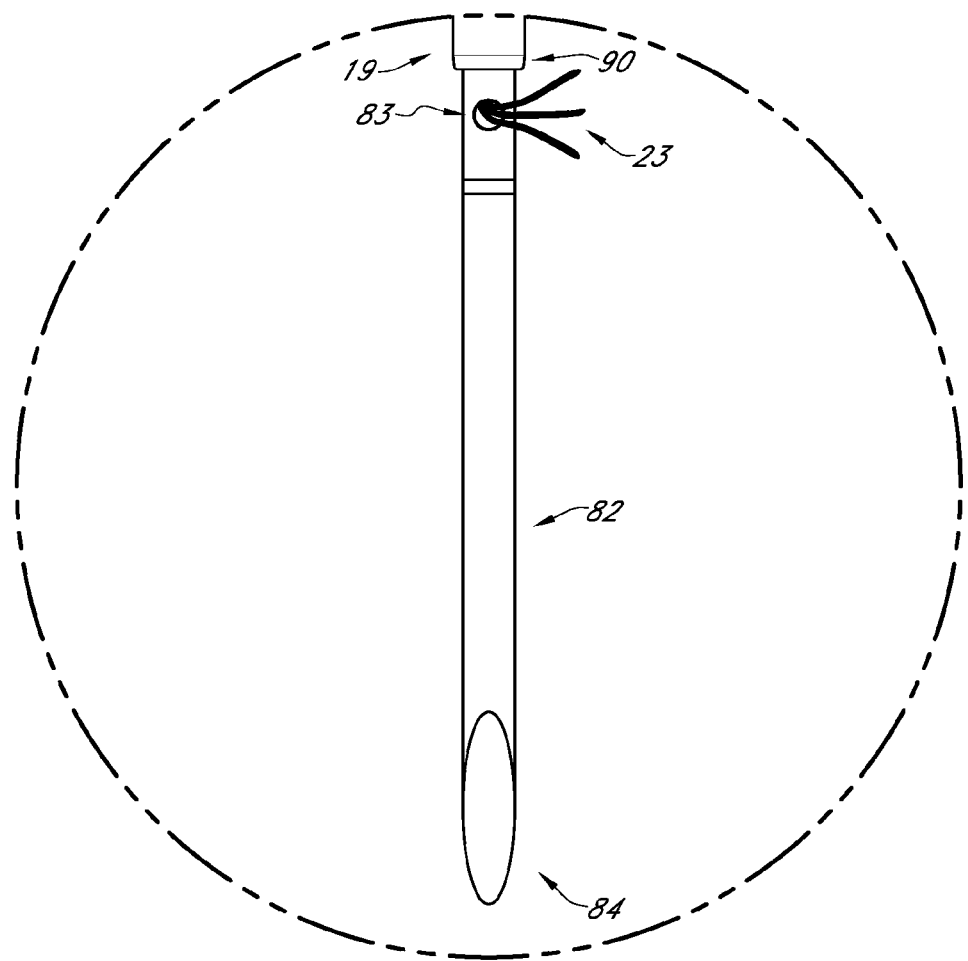

FIGS. 6A-C illustrates embodiments of the components of the sealant delivery device and the sealant delivery device assembly configured to apply a sealant along the length (e.g., the entire length or part of the length) of a tract made in tissue (i.e., a tissue tract) as the device is inserted into tissue. The components of FIGS. 6A-6C may be included together as a kit; for example, the user may receive a container which contains the housing sheath component 92, the tissue introducer component 82, and/or biosealant reservoir 85 (with or without biosealant). The kit may contain the components pre-assembled (i.e the tissue introducer coupled to the housing sheath component as a sealant delivery device assembly or assembled sealant delivery device) or unassembled. In one embodiment, the tissue introducer component of the sealant delivery device comprises a tissue introducer 82 comprising an articulable hub 81, a longitudinal lumen 82A having an interior surface and an exterior surface formed by a wall of material (e.g., as in a needle or tube), one or more ports 83 (a single port in preferred embodiments), and a distal tip 84 having or terminating in a sharp edge or point (e.g., tapering to a sharp point) for cutting through or piercing tissue, wherein distal tip 84 is positioned on a first end of longitudinal lumen 82A and the articulable hub 81 is positioned at an opposite second end of longitudinal lumen 82A (connected, preferably fluidly connected, to opening 80A), and wherein the one or more ports 83 are positioned on the longitudinal lumen 82A and between the distal tip 84 and the articulable hub 81. Articulable hub 81 is "articulable" (i.e., moveable) relative to the proximal housing sheath 21 of the housing sheath component, by including a jointed or other type of connection that allows for movement relative to the proximal housing sheath 21 in the assembled sealant delivery device. In preferred embodiments, the sealant is deposited into the longitudinal lumen 82A and applied to tissue through the one or more ports 83 as the device is inserted into the tissue tract. In preferred embodiments, the distal tip 84 is closed (i.e., sealed), is positioned distal of an open port 83, and forms a tract within the tissue as it is inserted into (e.g., traverses and/or moves through) tissue. Thus, in such preferred embodiments, a closed distal tip 84 provides for piercing through the tissue and prevents coring of tissue (e.g., as compared to an open distal tip). Furthermore, in some embodiments, the closed distal tip 84 may comprise a three-face bevel with different angles or a single bevel with two side-face cuts. In preferred embodiments, then, the tissue introducer 82 is so called because it has a sharp closed distal tip 84 which is used for piercing and creating the tract through the tissue (e.g., in preferred embodiments the chest wall, pleural space, and/or lung parenchyma). Accordingly, then, the tissue introducer, and at least the distal tip thereof 84, is preferably manufactured from a material of sufficient strength such that it does not decompose as it pierces and proceeds through the tissue (e.g., it is configured to pierce tissue and have enough rigidity to withstand the forces of the differing tissues). In certain embodiments, the tissue introducer 82 and at least the distal tip thereof 84 is manufactured from a hard plastic or metal substance.

The one or more ports 83 (referred to herein in its preferred embodiment as a single port) can be located on the distal, central, or proximal sections, relative to distal tip 84 or articulable hub 81 of the tissue introducer 82. Preferably port 83 is positioned proximal to distal tip 84, and distal from the articulable hub 81 (i.e., closer to distal tip 84 than to articulable hub 81). The port 83 is preferably located in the wall of the longitudinal lumen 82A of the tissue introducer 82. Additionally, port 83 can contain multiple holes or openings at differing angles relative to one another (e.g., multiple ports). For example, there may be a port 83 positioned at both the distal and proximal end of the longitudinal lumen 82A, or two or more ports can be positioned nearer to or further from distal tip 84 relative to articulable hub 81. The port(s) 83 can have any relative shape including but not limited to a circle, oval, notch, rectangle, square, triangle. Furthermore, the edges of the port 83 may be beveled, chamfered, or fileted to prevent tissue damage upon insertion or retraction. Additionally, the port may be formed at an off-angle relative to the longitudinal axis extending through the tissue introducer 82. In preferred embodiments, the port 83 is positioned about 0.015 to about 0.08 inches (e.g., any of about 0.15, 0.2, 0.3, 0.04, 0.05, 0.06, 0.07, or 0.08 inches) from (i.e., proximal to) the closed distal tip 84, and thereby distal from articulable hub 81. A radiopaque or echogenic marker may be placed in specific reference to the port 83, such as within the same lateral plane or offset a specific distance in a proximal or distal direction. The radiopaque marker may be in the form of a predetermined shape, letter, or arrow. More preferably, the radiopaque marker may comprise an annular ring of fixed width which encompasses the entire outer surface of the tissue introducer 82 (e.g., upon the exterior surface of the longitudinal lumen 82A). The radiopaque marker allows the user to locate the location of the port 83 while the device is located within the tissue via an imaging modality such as CT-imaging. X-Ray, ultrasound, or fluoroscopy.

In use, the sealant is extruded through port(s) 83 and deposited within the tract created by the closed distal tip 84 as it proceeds through (e.g., pierces) the tissue. Thus, in these embodiments, the closed distal tip 84 is creating the tract and the sealant is being deposited in that tract. In preferred embodiments, the sealant is initially deposited into the tissue tract slightly behind the closed distal tip 84 as the same pierces the tissue. However, in some embodiments, depending on the amount of sealant being injected into the tissue tract, the sealant may be deposited into the tract essentially as the tract is being formed by the closed distal tip 84, and in some cases may be applied just ahead of the closed distal tip 84 by virtue of pressure pushing sealant forward such that the leading edge of distal tip 84 is moving into and through essentially pre-deposited sealant as it pierces the tissue and forms the tract, especially as it nears the target tissue (e.g., lung tissue). This is advantageous because separate devices are not needed to both inject sealant and/or create the tract. The sealant can also, or alternatively, be deployed as the device is removed from the tissue.

In some embodiments, the closed distal tip 84 may be substituted by a distal tip 84 including at least one opening (i.e., distal tip 84 is not completely closed) through which sealant can exit through distal tip 84. In some such embodiments, sealant may be applied to the tract from both port 83 and distal tip 84. In such embodiments, sealant can be applied to the tissue tract at least slightly ahead of distal tip 84 with respect to tissue such that the leading edge of distal tip 84 is moving into and through essentially pre-deposited sealant as it pierces the tissue and forms the tract, especially as it nears the target tissue (e.g., lung tissue). In some such embodiments, sealant can also, or alternatively, be applied to the tract as the device is removed from the tissue.

As shown in FIGS. 6A-C and as referred to above, the tissue introducer 82 comprises an articulable hub 81 at a first end and a distal port 84 on a second end, the articulable hub 81 at a first end and a distal port 84 being connected (i.e., fluidly connected) such that fluid such as a sealant can flow through a channel in the articulable hub 81 and into the longitudinal lumen 82A of the tissue introducer, and therethrough to the distal port 84. In preferred embodiments, the wall of the longitudinal lumen (82A) can range from 0.003-0.006 inches (e.g., about 0.003, 0.004, 0.005, or 0.006 inches), and it may have an outer diameter ranging from 14 gauge-24 gauge (e.g., 14, 15, 16, 17, 18, 19, 20, 21, 22, 23 or 24 gauge), or 0.083-0.02225 inches. The articulable hub 81 also comprises an opening 80A (e.g., orifice or hole, optionally conical wherein the point of the cone is pointing toward the longitudinal lumen (82A) so that cross-sectional area distal to the longitudinal lumen (82A) is greater than that proximal to the longitudinal lumen (82A)) in fluid communication with the longitudinal lumen 82A. In some embodiments, the articulable hub 81 comprises an external surface including multiple ridges of raised material (81A) to assist the user in gripping and rotating the articulable hub 81 (and, therefore, the tissue introducer component and/or the assembled sealant delivery device). The articulable hub 81 also typically has an inverted bowl shape (81B) comprising at its upper surface a substantially flat or planar proximal face (81C) (e.g., proximal to a sealant reservoir and/or distal from longitudinal lumen 82A).

As mentioned above, in some embodiments, this disclosure provides an assembled sealant delivery device comprising the tissue introducer component and a housing sheath component 92 (e.g., trocar component). In preferred embodiments, the articulable hub 81 includes a female luer lock-type connection within the inverted bowl shape (81B) which encloses and connects to a proximal housing sheath 21 fastening section 96 that comprises a compatible male luer-lock type connection (which is itself described in more detail below). The luer lock-type connection is well-known for attaching devices, or units of devices to one another, in which threads on one of the devices and/or units engages opposing threads on the other device and/or unit to provide a leak-free seal, e.g., a rotating lock, and is commonly used in syringe devices (e.g., compatible with industry standard ISO 80369, ISO 594, DIN standard 1707:1996, and/or EN standard 20594-1:1993). Other suitable methods for connecting the articulable hub 81 and the proximal housing sheath 21 include but are not limited to screwing, press-fit, snap-fit, molding, and/or one or more adhesives. The assembled sealant delivery device is assembled by connecting (e.g., removably or reversibly connecting) the tissue introducer component and a housing sheath component (e.g., trocar component) using any such methods of connection.

Extending proximally from the articulable hub (81) flat/planar proximal face (81C) is columnar support 98, which can have a tapered cross section wherein the proximal cross-sectional area is smaller than the distal cross-sectional area. This columnar support can have the same cross-sectional area on the proximal and distal end with an open longitudinal lumen extending therethrough. Furthermore, extending in a substantially lateral and planar direction relative to the longitudinal lumen of the second columnar support 98 can be an articulable hub (81) fastening surface 99. This fastening section can comprise helical grooves which allow for a screw fastening coupling method. For example, the biomaterial reservoir 85 may comprise grooves which mate or align with grooves on second fastening surface 99 to provide a leak-free connection such that the sealant is in fluid connection with distal port 83.

An exemplary housing sheath component (92), to which a tissue introducer (82) component can be connected (e.g., removably or reversibly connected, or inserted and removed) in the assembled sealant delivery device is also shown in FIG. 6A. In preferred embodiments, the housing sheath component (92) includes a proximal housing sheath 21 connected to a distal housing sheath 19 that comprises a lumen extending from the proximal housing sheath 21 to the open distal end 90. The proximal housing sheath 21 includes a conical hole 94 at its proximal end connected to a lumen within the proximal housing sheath 21 that extends to housing sheath 19. In preferred embodiments, the housing sheath 19 can either have a straight orientation in which the cross-sectional area does not change, or a tapered design in which the cross-sectional area and/or wall thickness is greater at the proximal end relative to a distal end. The housing sheath 19 has a longitudinal lumen which extends from the proximal to distal end and allow the tissue introducer 82 to be housed therein. In some embodiments, proximal housing sheath 21 also comprises a septa (110 in FIG. 6F) therein which is oriented orthogonally to the longitudinal lumen of the housing sheath 19 and extends laterally across the proximal housing sheath. The septa interrupts the longitudinal lumen of the housing sheath 19 which extends from the proximal end of proximal housing sheath (i.e., opening 94 (e.g., orifice or hole, optionally conical wherein the point of the cone is pointing toward housing sheath 19 such that the cross-sectional area distal to the housing sheath 19 is greater than that proximal to the housing sheath 19) through to the housing sheath distal open end 90. In some embodiments, proximal housing sheath 21 comprises a body 97 that, in preferred embodiments, is tapered (i.e., has a proximal cross-sectional area greater than the distal cross-sectional area). Body 97 can further comprise ridges or grooves which are horizontally or vertically aligned, and/or may be tapered and/or conical in shape, to provide a better grip for the user (97A, e.g., "grips"). The geometry of the body 97 (e.g., the tapered section and/or grips) can be aligned with the orientation of the housing distal end 90; for example, the housing distal end 90 may comprise a tapered and angled end and the body 97 may be aligned such that it provides the user with visual and tactile feedback to relay the orientation of the housing distal end 90 to the user. Furthermore, body 97 may be aligned such that, in the assembled configuration of the sealant delivery device, it provides the user with visual and tactile feedback to relay the orientation of the port 83 of the tissue introducer 82 to the user as the same are being used in conjunction with one another. For example, in the assembled sealant delivery device, the port 83 on the tissue introducer 82 may be located along a longitudinal dividing line which symmetrically separates the body 97. The orientation of the port 83 relative to the body 97 can help the user more accurately deploy the sealant into the tissue. In some embodiments, a set of wings 100 extend in a substantially planar and lateral direction from the distal end of body 97 which act as a stop when applying a downward force on body 97, thereby preventing slipping. In some embodiments, columnar support 95 extends proximally from the body 97 and hub base 97B extends distally from the body 97. In preferred embodiments, columnar support 95 has the same cross-section at its distal end and proximal end with an open longitudinal lumen extending therethrough. The columnar support 95 provides an area for the articulable hub 81 to be coupled (e.g., removably or reversibly connected) to the housing sheath proximal end 21 without interfering or hitting the proximal end of body 97. Extending in a substantially lateral and orthogonally planar direction from the longitudinal lumen (i.e., conical hole 94) of the columnar support 95 is fastening section 96. The fastening section 96 comprises helical grooves which allow for a luer lock (e.g., screw) fastening coupling method to the tissue introducer component 82. For example, as discussed above, the grooves located on the inner surface of articulable hub 81 (i.e., within 81B) mate or align with grooves located on fastening section 96 to couple the tissue introducer 82 securely to the housing sheath component (i.e., comprising housing sheath proximal end 21 and housing sheath 19) to provide an assembled sealant delivery device.

In the assembled sealant delivery device, embodiments of which are illustrated in FIGS. 6B-C, the tissue introducer component 82 distal end 84 extends distally through the housing sheath distal end 90 such that the port 83 and distal end 84 extend therefrom (FIG. 6C). The housing sheath distal end 90 can comprise a tapered or angle tip to reduce the step or transition between the housing sheath 19 and the tissue introducer 82 and is open to allow the tissue introducer 82 (specifically, port 83 and distal tip 84) to extend therethrough and into the tissue and/or tissue tract in the assembled form of the sealant delivery device. In some embodiments, the wall of housing sheath 19 (i.e., surrounding the lumen) can range from 0.003-0.008 inches and an outer diameter ranging from about 13 gauge to about 23 gauge (e.g., about any of 13, 14, 15, 16, 17, 18, 19, 20, 21, 22, or 23 gauge), or about 0.095 inches to about 0.02525 inches (e.g., about any of 0.095, 0.085, 0.075, 0.065, 0.055, 0.045, 0.035 or 0.025 inches). It should be understood that the sizes of the tissue introducer and housing sheath described herein can smaller or larger without departing from the scope of the invention, as long as the tissue introducer 82 (i.e., the longitudinal lumen (82A) thereof) can be positioned within the housing sheath 19 (see, e.g., FIG. 6B) in the assembled form of the sealant delivery device. Thus, the outer diameter of the longitudinal lumen (82A) must be less than that of the housing sheath 19, and the inner diameter of the housing sheath 19 must be greater than that of the longitudinal lumen 82A. The housing sheath 19 can also contain graduated marking which may or may not be radiopaque along its length to indicate the depth of insertion to the user. Furthermore, the housing sheath 19 and/or tissue introducer 82 can contain a lubricous coating to aid insertion into tissue such as a hydrophilic polymer located on the inside or outside of the sheath. As mentioned above, in use the tissue introducer 82 is positioned within the housing sheath 19 which surrounds substantially the entire length of the tissue introducer 82 (i.e., the longitudinal lumen (82A) thereof) except that at least the closed distal-tip 84 and port 83 extend therefrom (FIGS. 6B and 6C). Thus, the housing sheath 19 helps provide rigidity and stability to the tissue introducer 82.

In use, a sealant reservoir 85 is typically tissue introducer proximal end (80) is sealant reservoir 85 (FIGS. 6A-B). The sealant reservoir 85 may be in any suitable form, such as a syringe, IV bag and/or line, deformable reservoir, or the like, which can be used to manually inject the sealant 23 (e.g., by applying pressure upon the reservoir such as be squeezing or pressing the same), and/or an automatic syringe or similar device that can automatically extrude the sealant 23 upon entry into the tissue (including in some embodiments any required software and computer for directing such a process). Manual and automatic processes may also be combined. Thus, in some embodiments, the syringe may include a plunger and tubular reservoir, wherein the plunger is mechanically activated to apply a compressive pressure to the tubular reservoir thereby extruding material from within the reservoir. The sealant reservoir 85 may have multiple lumens or compartments to hold multiple sealants or cross-linkable materials, allowing full control over which sealants are extruded. Additionally, the sealant may be located entirely within the inner lumen of the tissue introducer 82 (82A). The sealant reservoir can be coupled to the delivery sheath proximal end 80 by any suitable technique, including but not limited to screwing (e.g., a luer lock), press-fit, snap-fit, molding, and/or adhesive. By applying pressure to or through the reservoir 85, the sealant 23 is delivered through the longitudinal lumen (82A) of the tissue introducer 82 and extruded through the port 83. The fluid injection mechanism can be mechanical (syringe, squeezed using hands, spring loaded plunger) or electrical actuation. This device allows the user to control when and where the sealant is extruded and allows for the sealant to be applied before, during, and after the device is inserted into the tissue. For example, it may be desirable to apply the sealant automatically upon entry into the tissue using an automated sealant delivery mechanism attached to the reservoir. Alternatively, or additionally, the sealant 23 may be delivered manually via external pressure placed on the reservoir. In some embodiments, a pressure sensor may be incorporated near or on the distal end 84 of the tissue introducer 82 which may send a signal to the automated sealant delivery mechanism attached to the reservoir 85 to extrude a sealant 23 in response to a pressure.

FIGS. 6B and 6C further illustrate the proximal ends of both the tissue introducer 82 and the housing sheath 19 in the assembled form of the sealant delivery device. As illustrated in FIG. 6B, the assembled device provides tissue introducer 82 (i.e., at least port 83 and closed distal tip 84) protruding from the distal end of the housing sheath 19, the articulable hub 81 is coupled to the housing sheath proximal end 21, and optionally reservoir 85 is fluidly connected at tissue introducer proximal end 80. FIG. 6C shows a magnified view of the distal end of the assembled device, showing tissue introducer 82 (including port 83 and distal tip 84) extending from the distal end 90 of housing sheath 19.

Figure 6D:
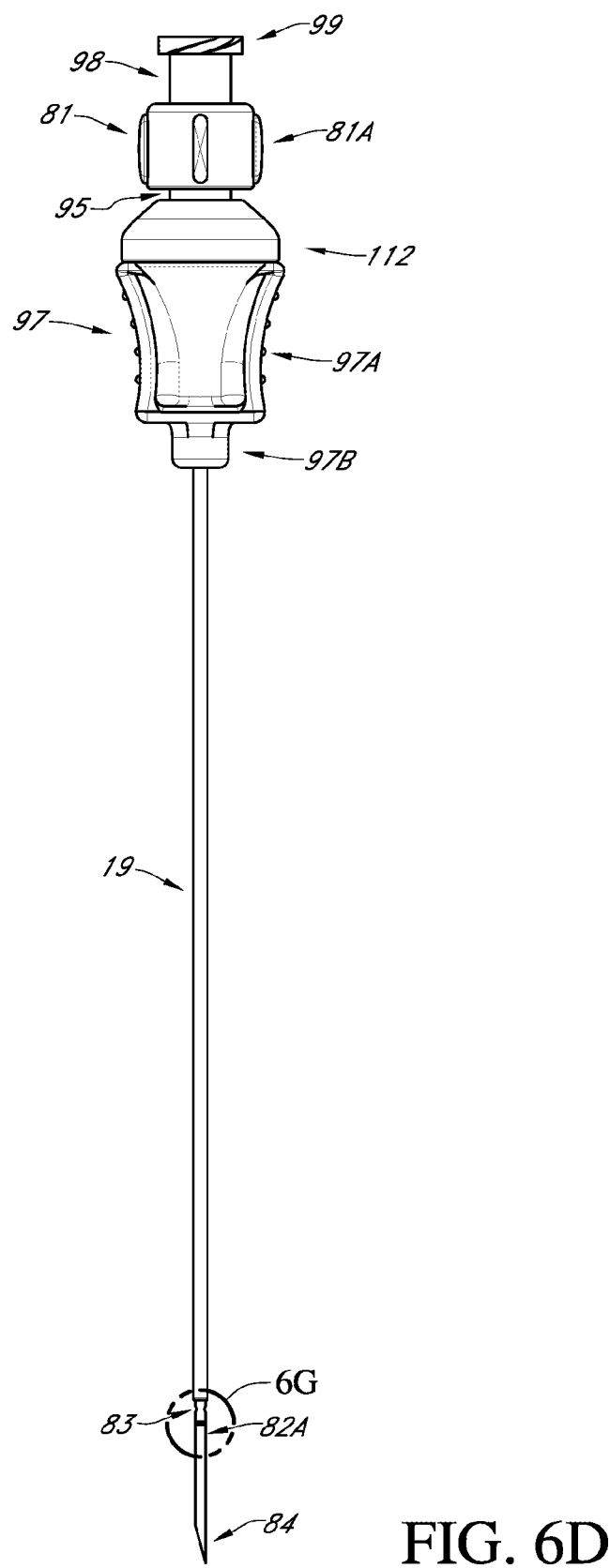
Figure 6E:
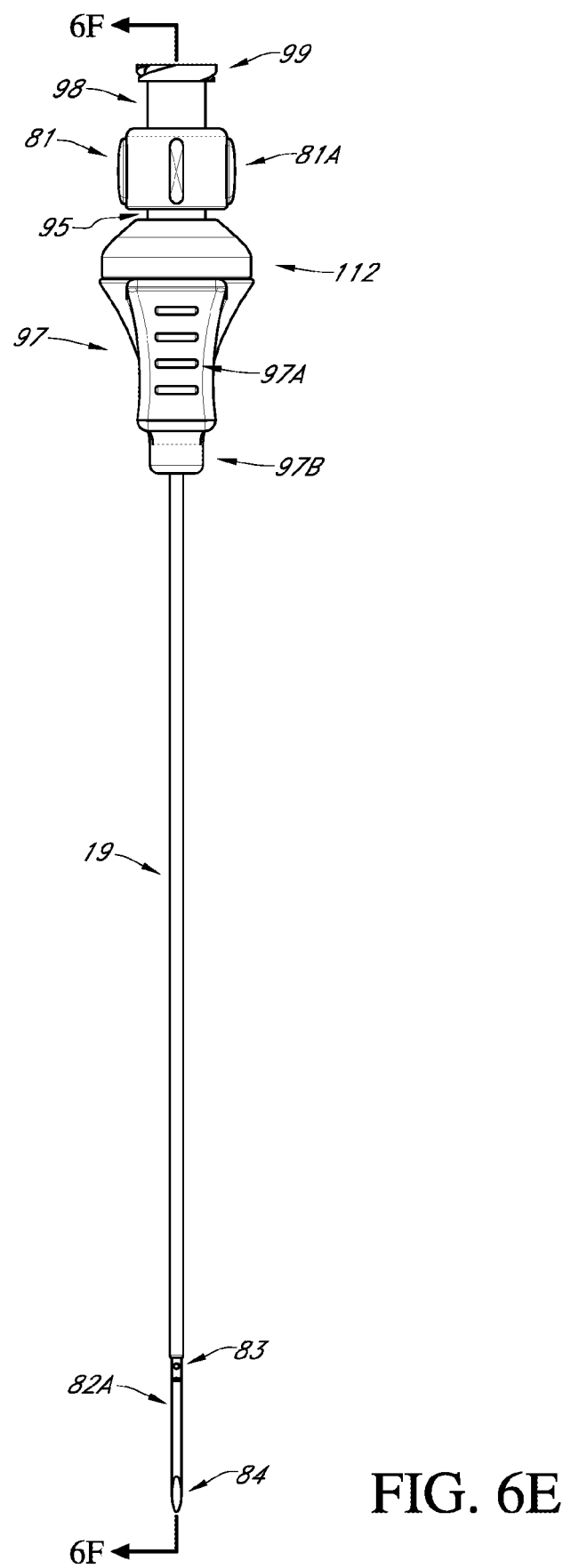
Figure 6F:
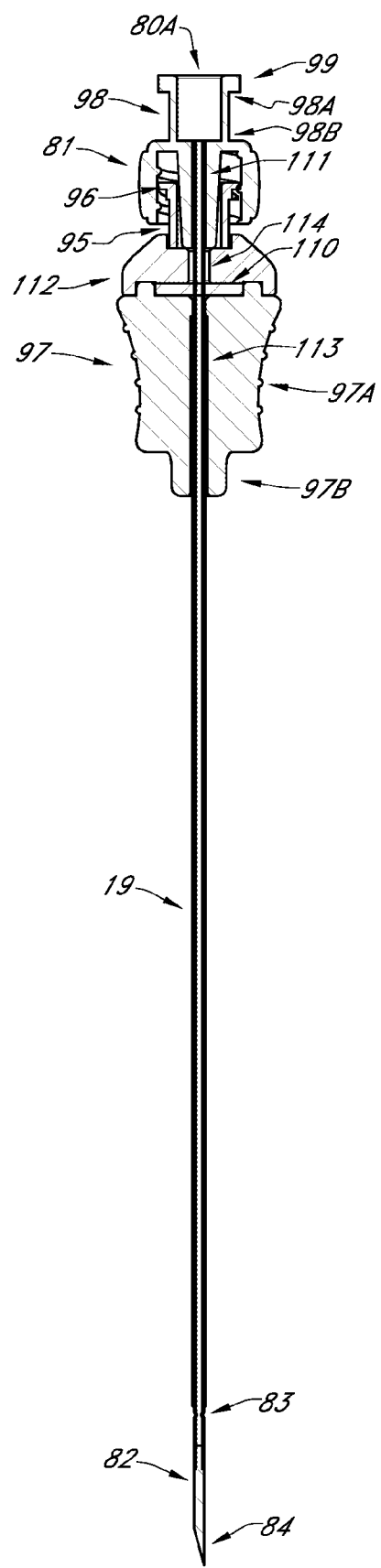
Figure 6G:
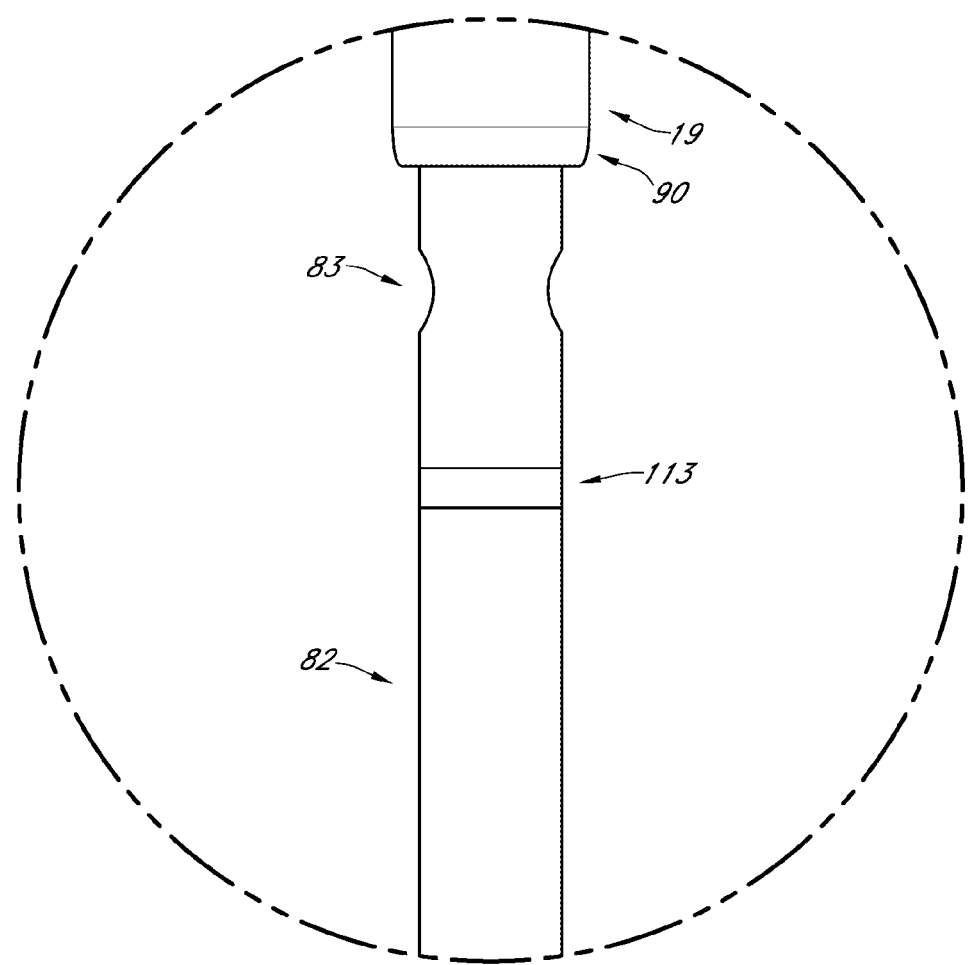

FIGS. 6D-F further illustrate an exemplary assembled form of the sealant delivery device, including additional preferable features of the articulable hub 81 and the housing sheath proximal end 21. As shown in FIGS. 6D-E, the assembled sealant delivery device comprises a tissue introducer 82 component having an articulable hub 81 with stylet hub 99 and columnar support 98 is connected (e.g., removably or reversibly connected) to the housing sheath component 92 including proximal housing sheath 21 and housing sheath 19, such that substantially the entire length of the tissue introducer 82 (i.e., the longitudinal lumen (82A) thereof) is within housing sheath 19 where at least the closed distal-tip 84 and port 83 extend therefrom. In these embodiments, the exterior of the articulable hub 81 includes raised sections of material or grips 81A which can be in the form of longitudinal ridges and/or raised dots extending outwardly from the surface of the articulable hub 81. The grips 81A assist the user with creating enough torque to securely fasten or couple the components together. In some embodiments, proximal housing sheath 21 comprises a proximal bulbous housing 112, a body 97, raised ridges 97A (e.g., providing grip assistance to the user), and hub base 97B. In preferred embodiments, at least body 97 is made of a translucent material.

FIG. 6F provides additional features of a preferred embodiment of the assembled sealant delivery device. As exemplified therein, the fastening surface 99 (which surrounds conical hole 80A) transitions to the second columnar support 98 which is integrally connected to the articulable hub 81. The interior of the articulable hub 81 has an inverted bowl-like shaped configuration with helical ridges lining the wall to provide a screw or luer-lock fastening mechanism to the fastening section 96/columnar support 95 of the proximal housing sheath 21. In this preferred embodiment, the articulable hub 81 comprises a first needle guide 111 which extends in a tapered fashion from the distal end of the second columnar support 98 (e.g., extending toward the bulbous housing 112 of the proximal housing sheath 21). The tapered orientation of the needle guide 111 allows for smooth flow of the sealant, thereby reducing the pressure that would be experienced by the user during insertion of the tissue introducer 82 component into the housing sheath component 92. The second columnar support 98 may comprise a constant cross-sectional area from its distal to its proximal end, and/or it may have a tapered orientation where the cross-sectional area of the proximal end is greater than the cross-sectional area of the distal end. The articulable hub 81, first needle guide 111, second columnar support 98, and fastening section 99 create a monolithic or integral piece in which the longitudinal lumen 82A runs through the first needle guide 111 and is flush with the distal end of the second columnar support 98B. Referring to housing sheath device 92 of the assembled sealant delivery device, a bulbous housing 112 is located proximally the body 97. The bulbous housing can be sealed to the proximal end of the body 97 with the septa 110 located therebetween. Additionally, in preferred embodiments, the bulbous housing 112 is a transparent or translucent material to indicate to the user that fluid (e.g., sealant) is flowing through the septa. The bulbous housing 112 may contain a marking or line indicating the orientation of the port 83. For example, the line may be in a straight-line with the port 83 to indicate to the user to location and orientation of the port when the device is located within the tissue. Furthermore, a marking or line may also be located on the tissue introducer proximal end 80 to indicate the orientation of the port(s) 83. For example, the line may be in a straight-line with the port to indicate to the user to location and orientation of the port when the device is located within the tissue. In preferred embodiments, bulbous housing 112 further comprises a second needle guide 114 with a tapered orientation (e.g., tapered toward the distal end 90 of housing sheath 19 and distal port 84 of tissue introducer 82) located within and in direct alignment with the first needle guide 111. The second needle guide 114 improves the process of inserting the tissue introducer 82 component (i.e., 82A thereof) within the housing sheath 19. The second needle guide 114 is in direct contact with the proximal end of the septa 110. Located distal of the septa 110 is housing sheath 19, which is encased or enclosed by body 97 (which in preferred embodiments comprises grips 97A that assist the user with applying adequate force to insert the device into tissue). On the distal end of gripping surface 97 is gripping surface base (hub base) 97B having a smaller cross-sectional area than gripping surface 97. The gripping surface 97 is coupled to the bulbous housing 92 with the septa 112 located therebetween, which form an integral component. Optionally, the housing sheath 19 can include a radiopaque marker 113 located proximally, distally, or in-line with the distal port 83. The radiopaque marker can be a band which extends circumferentially around the tissue introducer 82 (i.e., 82A). The marker can be made of materials including but not limited to radioisotopes, iodine and iodine compounds, metals such as gadolinium, gold, platinum, silver, or tantalum, barium sulfate powder, polymers, and/or a combination thereof. This embodiment can therefore contain a proximal indicator for the port 83 and/or housing distal end 90 including a line or marking or the bulbous housing 112 and/or the tissue introducer proximal end 80. Furthermore, the gripping surface 97 may also have a specified alignment to convey tactual or visual feedback to the user regarding the alignment relative to the port and/or housing distal end. The sealing mechanisms for connecting the different parts of the components of the sealant delivery device can include but are not limited to screwing, press-fit, adhesives, UV-cured adhesives, molding, extrusion molding, and/or casting.

Regarding the manufacturing of the components of the sealant delivery device (e.g., as illustrated in FIG. 6F), the bulbous housing 112 and gripping surface 97 can be manufactured by 3D printing, for example using an Objet™ Printer. The bulbous housing 112 and gripping surface 97 and septa 110 are separable components which can then be coupled in their final configuration as a unit. The septa 110 is placed within a circular indent located in the proximal end of gripping surface 97. Then, the bulbous housing 112 can then coupled to the proximal end of gripping surface (i.e., body 97) along a circumferential ridge which spans the gripping surface 97 creating an integral housing sheath proximal end 21. The parts can be coupled by screwing, press-fit, snap-fit, molding, and/or adhesive. The housing sheath 19 is then inserted through a hole which extends from the gripping surface base (hub base) 97B to the proximal end of the gripping surface 97. The housing sheath 19 can be coupled to the housing sheath proximal end 21 by screwing, press-fit, molding, and/or adhesive. Additionally, the articulable hub 81 can be produced by 3D printing using, for instance, an Objet™ Printer. Subsequently, the longitudinal lumen 82A is inserted through the first needle guide 111 until it is flush with columnar support distal end 98A. The longitudinal lumen can be coupled via screwing, press-fit, molding, and/or adhesive.

Figure 7A:
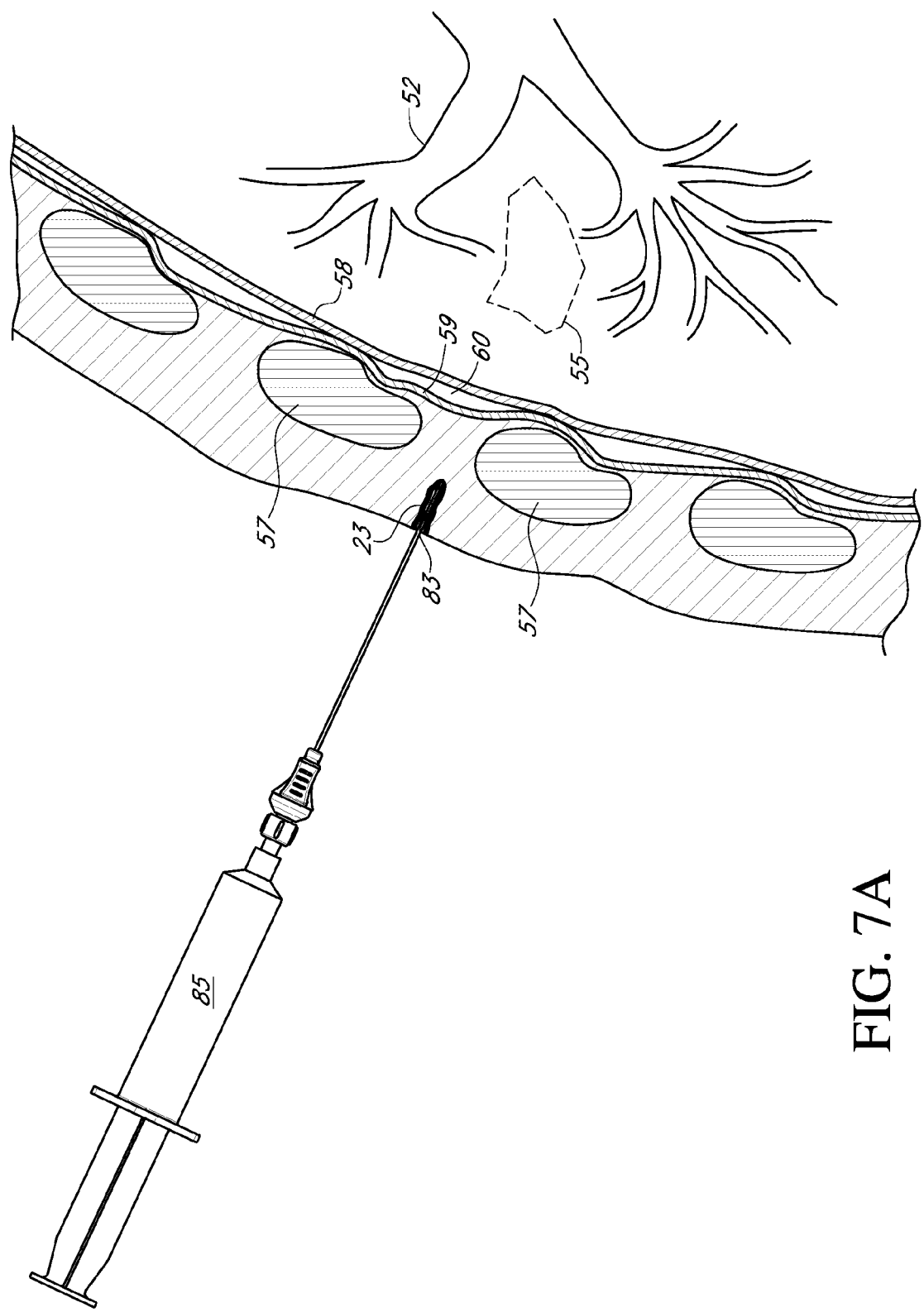
FIGS. 7A-7C illustrate the device of FIGS. 6A-E as used in the procedure.
Figure 7B:
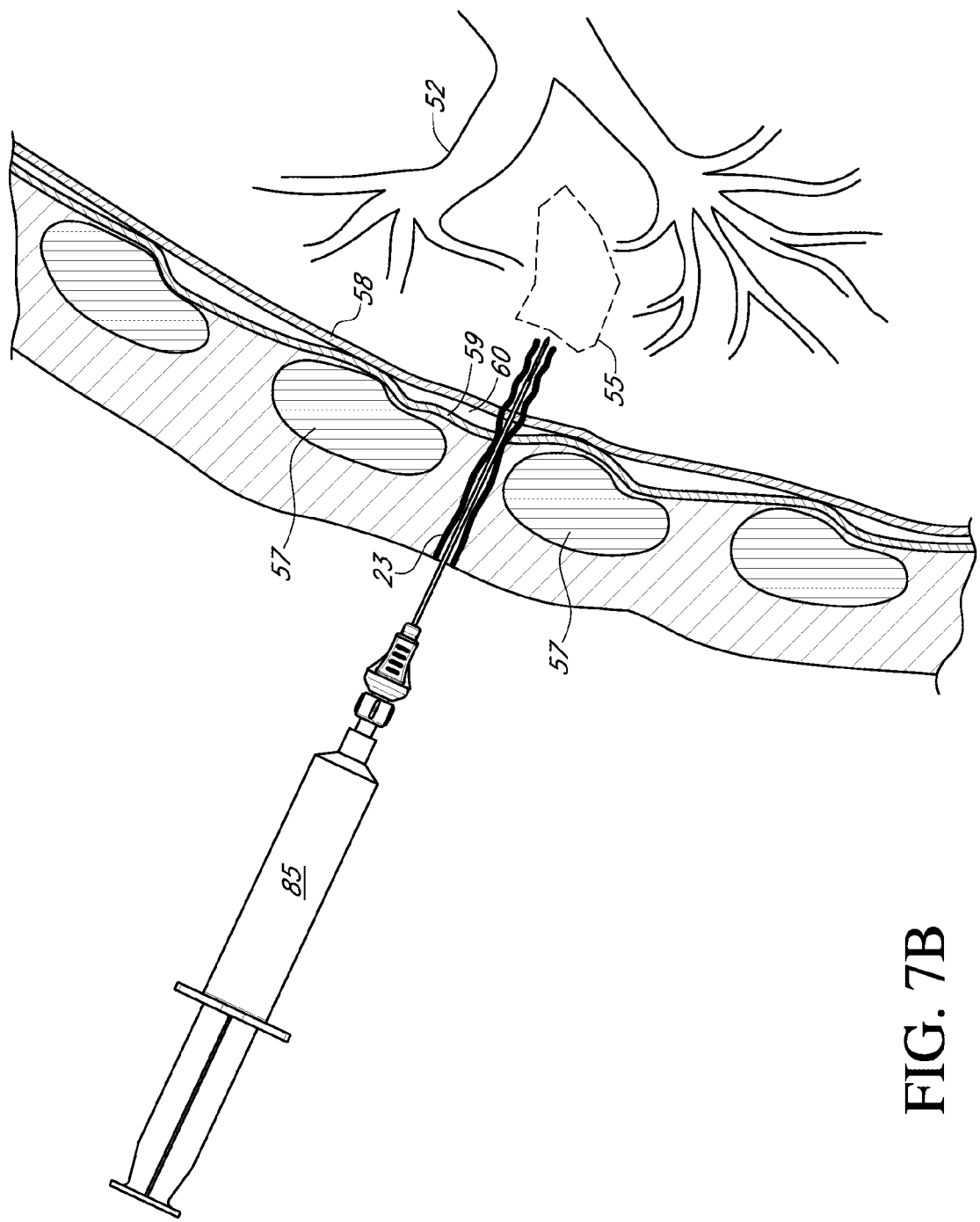
Figure 7C:
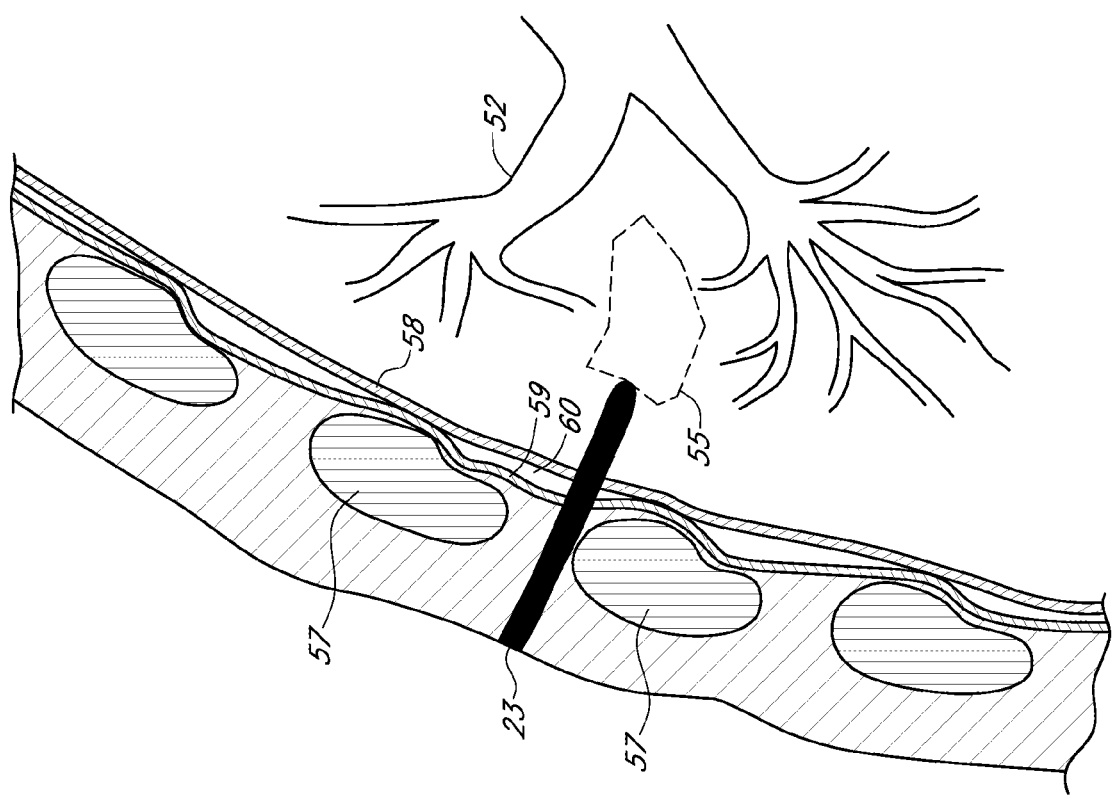

FIGS. 7A-7C illustrate the device of FIG. 6 as used in the procedure. Referring to FIG. 7A, the sealant 23 can be immediately extruded from the port 83 which is in fluid communication with reservoir 85 immediately upon entry into the tissue. Alternatively, the sealant 23 can be deployed after the pleural space 60 is compromised and the tissue introducer 82 enters into the lung parenchyma. Referring to FIG. 7B the sealant lines the entire length of the tract upon reaching the desired location such as a lung lesion 55. FIG. 7C illustrates that upon removal of the device the entire needle tract is sealed with sealant 23. The sealant 23 deployed may include but not be limited to materials in the form of a liquid, gel, solid, microsphere, sutures, glue, shape memory staples. The sealant can be tuned to swell at a specific rate or change material properties including but not limited to adhesiveness, viscosity, liquidity, density, hardness, or flexibility in reaction to certain stimuli including but not limited to pH, fluid, blood, saline, temperature, light, electron-beam, gamma-radiation, UV, DNA, enzymes, and other suitable initiators. Additionally, another cross-linking material may be added to increase or decrease the reaction time. Multiple sealants may also be injected at the same time. Furthermore, the sealant 23 can have a composition which allows it to travel up the length of the tract when extruded due to the pressure applied by the surrounding tissue to the device.

Figure 8A:
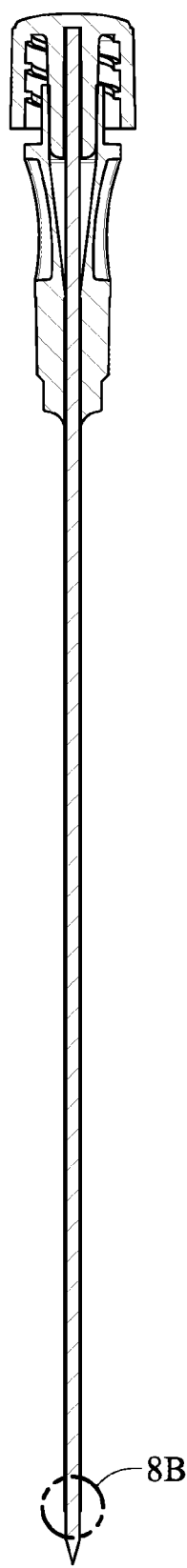
FIG. 8A-B illustrates another device adapted to deploy a sealant throughout the length of the tract at any time during the procedure.
Figure 8B:
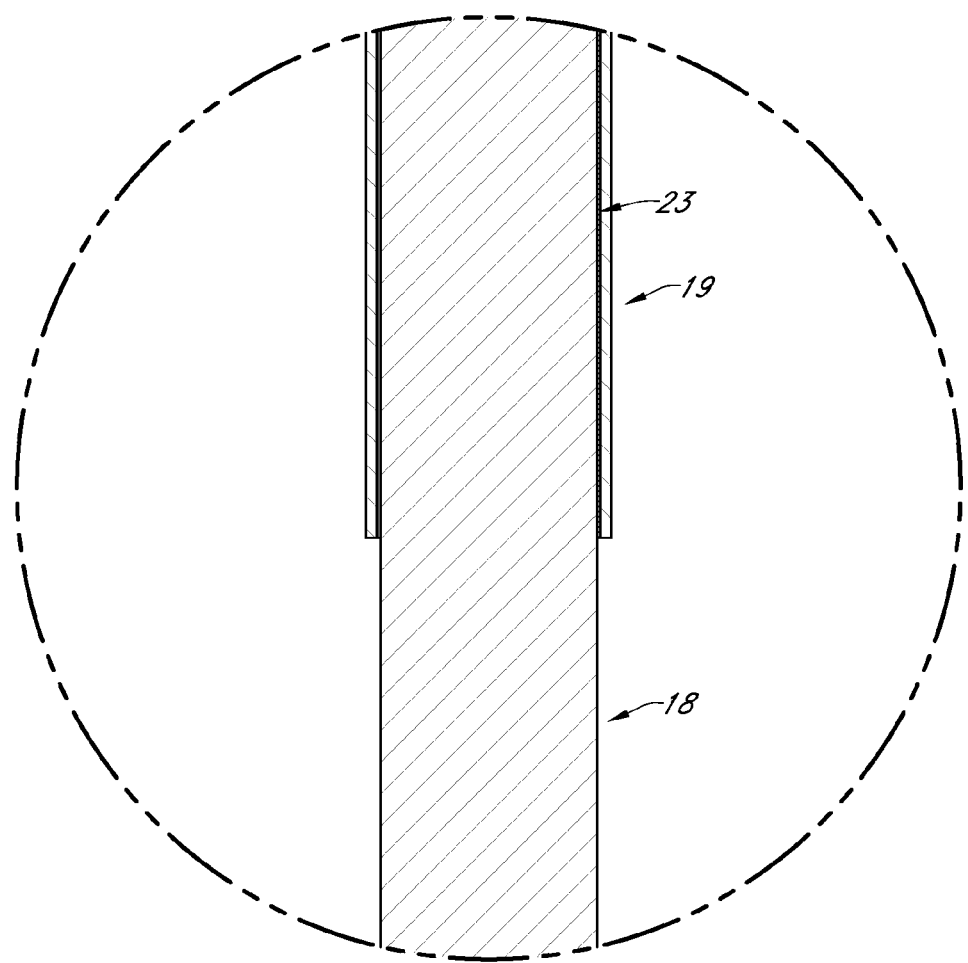

FIG. 8 illustrates another device of the present invention configured to apply a sealant throughout the length of the tract. In this embodiment, sealant 23 is extruded between the space defined by the tissue introducer 18 and the housing 19. The reservoir 85 is able to connect to the proximal housing sheath 21 and extrude sealant between the tissue introducer 18 and housing 19. Alternatively, the sealant 23 can be deployed after the pleural space 60 is compromised and the device enters into the lung parenchyma. This embodiment comprises a solid tissue introducer 18 which has a distal tip extending distally from the distal end of the housing 19.

Figure 9A:
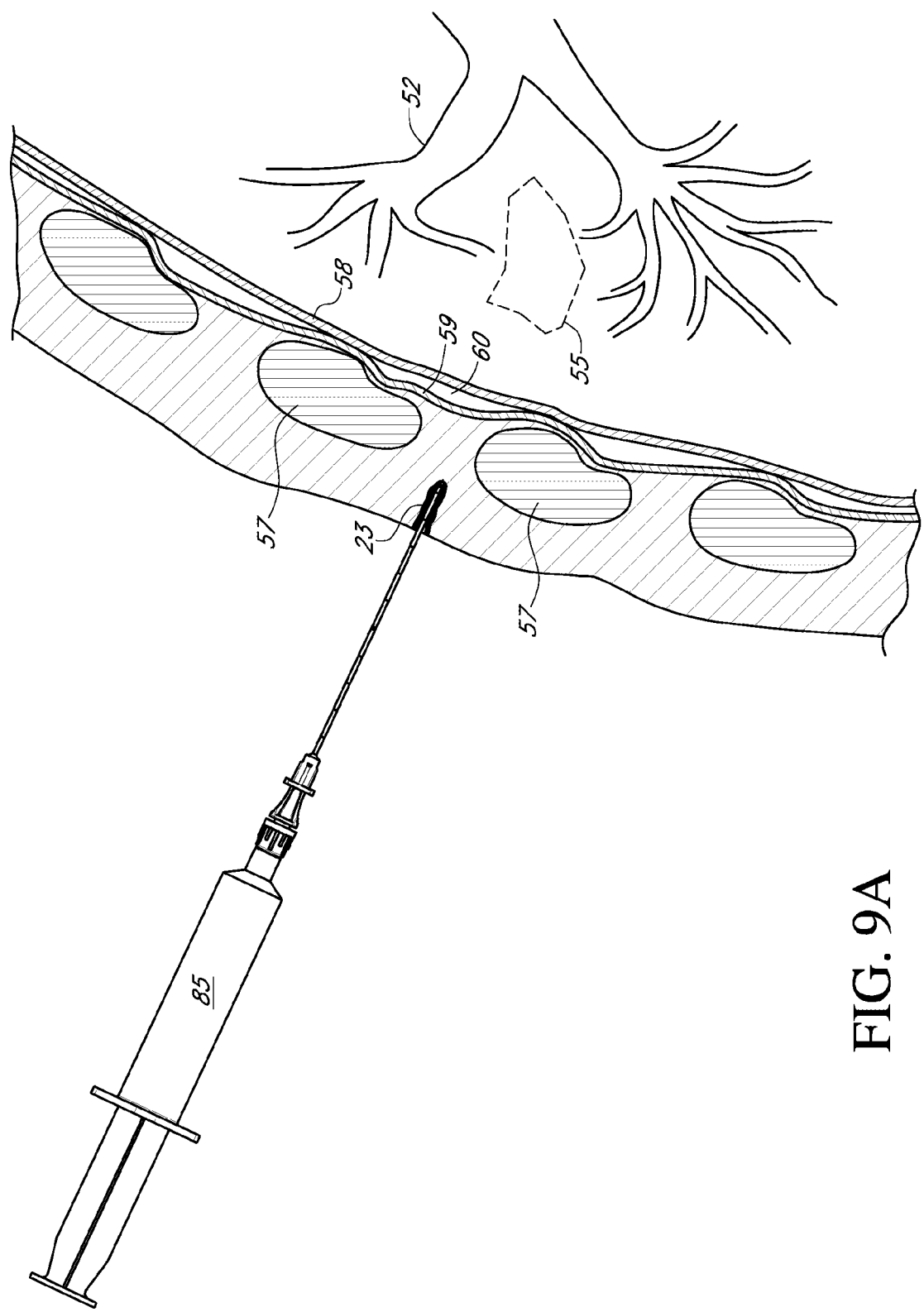
FIGS. 9A-9C illustrate a device adapted to deploy a sealant throughout the length of the tract at any time during the procedure.
Figure 9B:
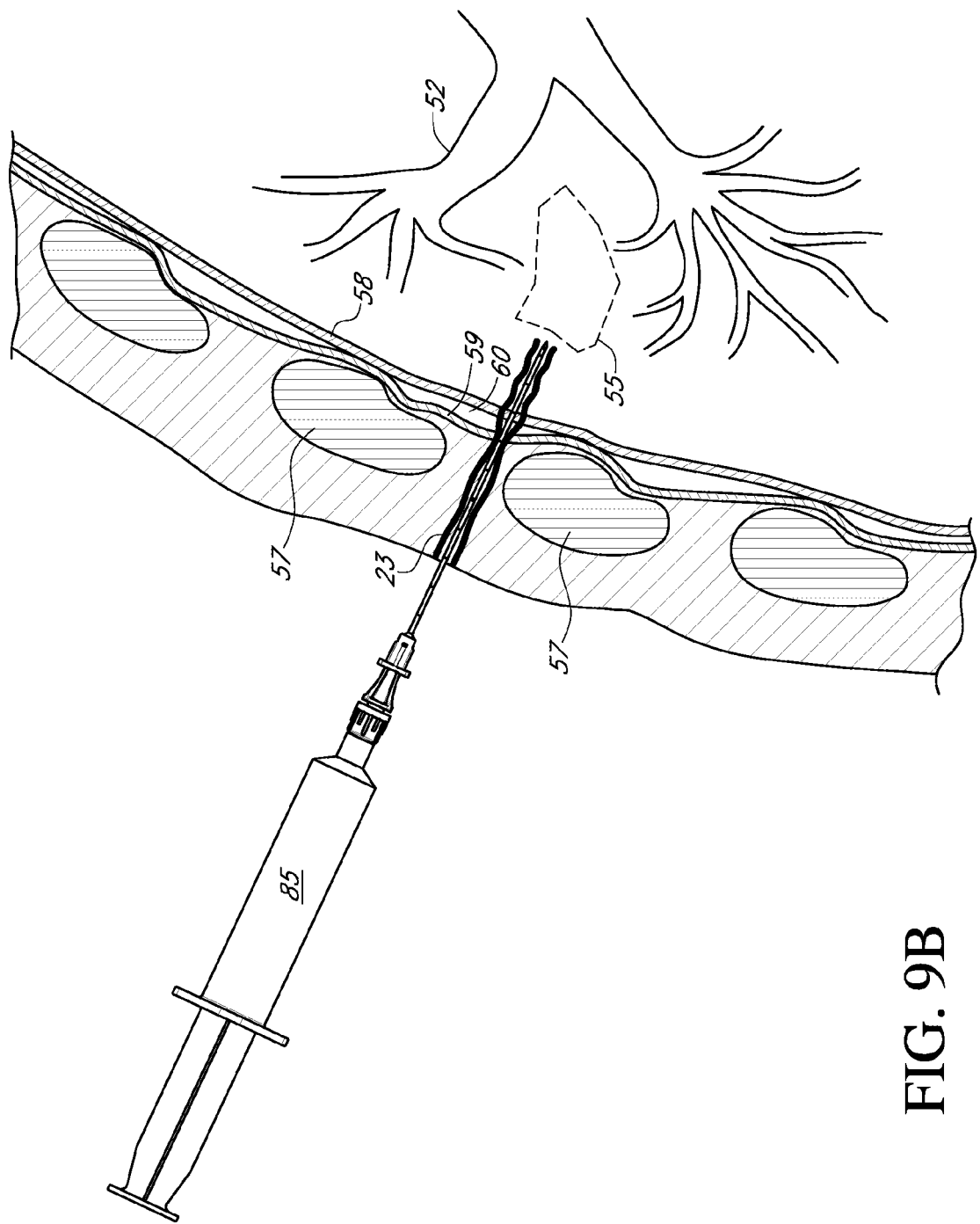
Figure 9C:
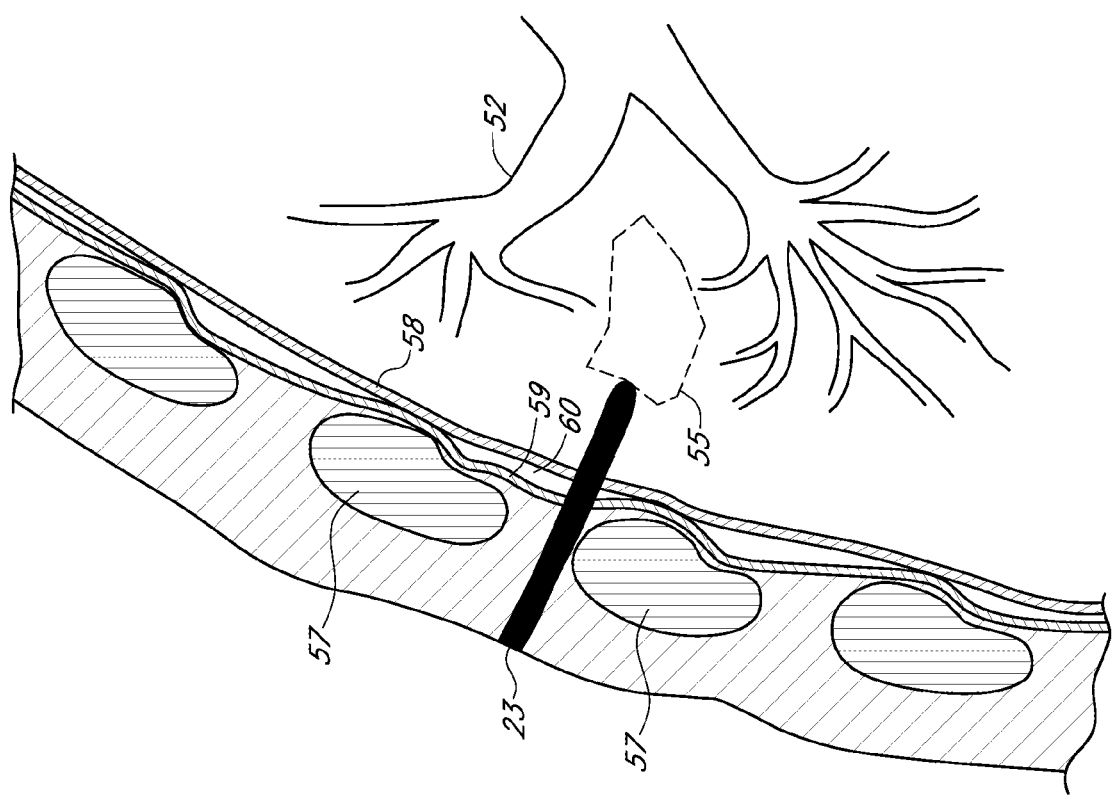

FIGS. 9A-9C illustrate the device of FIG. 8 as used in the procedure. Referring to FIG. 9A, the sealant 23 can be immediately extruded between the spaced defined by the tissue introducer 18 and the housing 19. Referring to FIG. 9A, the sealant is extruded upon immediate entry into the tissue. Referring to FIG. 9B, the sealant lines the entire tract upon reaching the desired location such as a lung lesion 55. FIG. 9C illustrates that upon removal of the device the entire tract is sealed with sealant 23 thereby preventing the flow of fluids or gas through the tract.

Figure 10A:
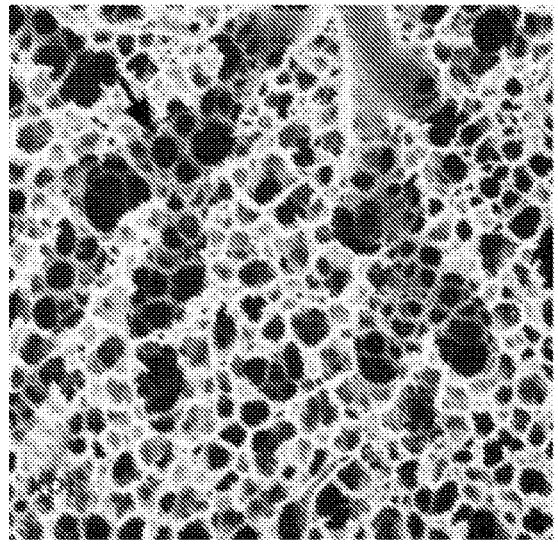
FIGS. 10A-10B are scanning electron microscope images of healthy and emphysematous lungs.
Figure 10B:
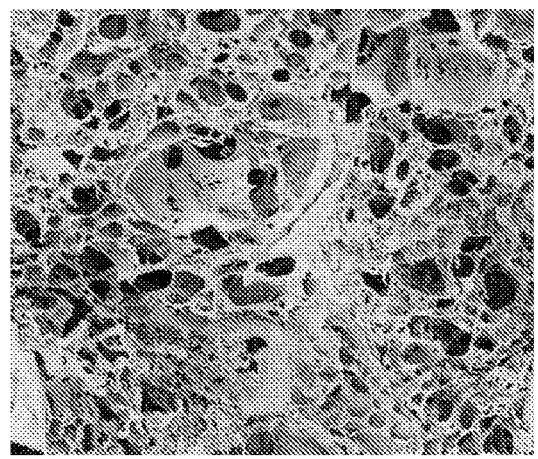

FIGS. 10A-10B illustrate the tissue characteristics of healthy versus emphysematous lung parenchyma. FIG. 10A shows a healthy lung which is characterized by a spongy/porous nature. The lung parenchyma is primarily formed from type I and III collagen which help provide structure to the alveolar walls. The lung parenchyma also comprises elastin fibers which are mechanically connected to the collagen and aid with the volumetric expansion and contraction of the lung during breathing. Emphysema is a disease which breaks down the collagen and elastin structures and therefore weakens the structure of the lung. As shown in FIG. 10B, emphysematous lungs lose their proportional porosity and result in larger pores with frayed tissue edges. Additionally, the lost elasticity of the lungs in emphysematous patients results in residual air being trapped in the alveolar ducts with an inability to expel the air due to damaged collagen and elastin fibers. The residual air, upon being accessed via a biopsy tool or other trauma, will attempt to travel to the pleural space through the needle tract and increases the risk of inducing a pneumothorax. Additionally, the air is capable of traveling up the needle tract while the tissue collection device is within the tissue, necessitating the need for a sealant to be present upon entry into the tissue.

FIG. 11 illustrates the potential locations for air entry during a percutaneous transthoracic biopsy. The main locations include the entry location through the skin and the entry location into the lung tissue. It is desired that the sealant deployed will successfully block fluids and gases transporting through or between both entry locations.

Transthoracic lung biopsies typically require multiple needle insertions across the pleural membranes ("pleural crossings") and other tissues to ensure the device is on the correct trajectory to the target site. A significant risk factor for pneumothorax is the number of pleural crossings which increases with each needle reinsertion, or alteration in its trajectory through the pleural membrane and/or other tissues. A significant benefit of the device provided herein is reduced risk of pneumothorax due to continuous tract sealing. Using the devices described herein, therefore, multiple needle insertions can be performed without increasing the risk of pneumothorax.

Figure 12:
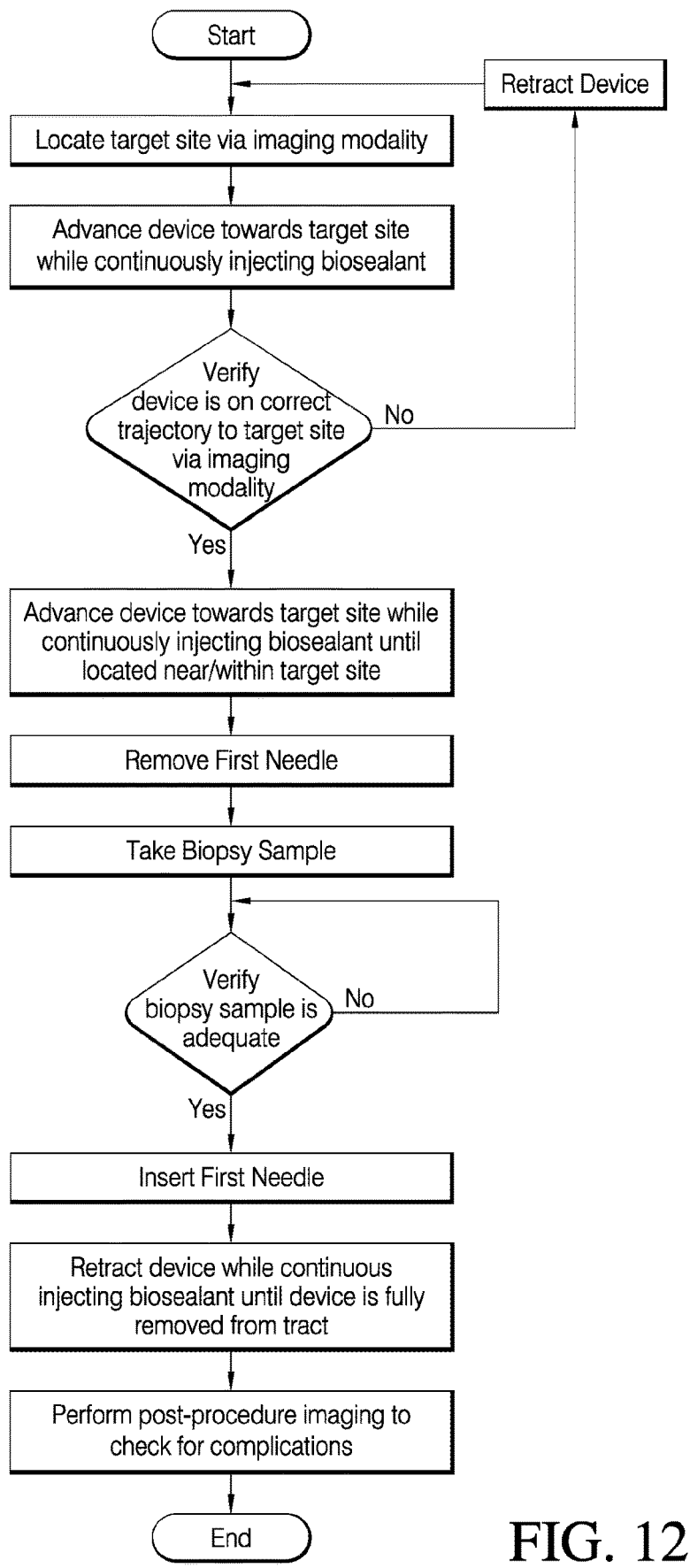
FIG. 12 illustrates the steps of an exemplary method for using the devices described herein.

FIG. 12 is an example workflow of the proposed device. A target site can be located via an imaging modality including but not limited to magnetic resonance imaging (MRI), computed tomography (CT) scan, X-Ray, and/or ultrasound. Upon insertion of the device provided herein into the tissue, biosealant can be deployed (e.g., preferably continuously) into the tissue and/or pleural membranes to act as a sealant to internal and/or external gases and/or fluids. The user can then ensure the device is on the correct trajectory to the target site by taking another image. If the second image confirms that the device is not on the correct trajectory the device can be retracted while deploying biosealant which effectively seals the tract and reduces the risk of a complication forming. Thus, the biosealant remains within the tract(s) following retraction, thereby ensuring the tracts remain sealed to internal and/or external gases and/or fluids. Alternatively, if the device is on the correct trajectory it can be advanced while deploying (e.g., continuously) biosealant until the target site is reached and the device is either within the target site or abuts the target site. Upon reaching the target site, the first needle is removed and a standard biopsy gun is inserted through the second needle and used to take a sample of the target site. Alternatively, an ablation probe could be used to insert through the second needle and ablate a target site. Using the device described herein, multiple samples may be removed from the tissue (the taking of each sample being referred to as a "pass") to ensure a quality tissue sample is extracted for more precise pathological analysis. Upon completion of the biopsy, the first needle is reinserted and coupled to the second needle. The device is then retracted and biosealant deployed (e.g., continuously) to the tract until the device is completely removed from the tissue. After the device is completely removed, a post-procedure image can be taken of the patient (e.g., the lung and surrounding tissue) to check for complications including but not limited to pneumothorax or hemothorax. Upon confirmation that there are no observed complications, the procedure is completed. While not deviating from the spirit or scope of the invention it should be recognized that the preferred embodiment can be used to provide a seal against any transthoracic device which creates a tract connecting the pleural space to the outside environment through the chest wall or connects the pleural space to the internal tissue of the lung or connects the internal tissue of the lung through the pleural space through the chest wall. The device described is used to seal a tract upon immediate insertion into the tissue area preventing any fluid from migrating. Therefore, the present device can be used with biopsy tools, ablation tools, and other transthoracic devices. Furthermore, the preferred embodiment may be used to seal the tract upon entry to a target location, the inner needle or tissue introducer may be removed leaving the second needle or housing sheath in place. An ablation tool using RF, microwave, cryogenic, ultrasound, x-ray, electroporation or other energy modality may be inserted through the second needle or housing sheath and treatment may be performed on the target site. After treatment the inner needle or tissue introducer may be reinserted into the second needle or housing sheath and the sealant may be applied as the device is removed. The integration of the preferred embodiment with other treatment methods including biopsies, ablation tools, and drug delivery devices provides versatility and a standardized method to seal a tract to prevent complications. More preferably the preferred embodiment provides a standardized solution to seal a transthoracic tract for any transthoracic treatment modality. While not deviating from the spirit or scope of the invention it should be recognized that the preferred embodiment can be used to provide a seal against any transthoracic device which creates a tract connecting the pleural space to the outside environment through the chest wall or connects the pleural space to the internal tissue of the lung or connects the internal tissue of the lung through the pleural space through the chest wall. The device described is used to seal a tract upon immediate insertion into the tissue area preventing any fluid from migrating. Therefore, the present device can be used with biopsy tools, ablation tools, and other transthoracic devices.

The devices as described above aid in the prevention of pneumothorax. Particularly, the devices are able to apply a sealant during the procedure which is able to be deposited the length of the tract. Additionally, the sealant has the ability to be delivered before the therapeutic of diagnostic procedure, during the procedure, or after the procedure. More importantly, FIGS. 7A-7C and FIGS. 9A-9C illustrate devices in which the amount of sealant can be selectively applied by the user. Also, all of the devices listed above are able to be interchangeable and modular with standard biopsy tools which include a biopsy gun, trocar, and stylet. For example, the tissue introducer 18 can replace the stylet of the standard biopsy tools and be perform a similar function throughout the procedure with the added benefit of the ability to supply a sealant at the users discretion. The device also allows the user to identify when they have breached the pleural space because the force required to extrude sealant will lessen due to negative pressure within the pleural layers and the porous and less-dense tissue located within the lung. Therefore the resistance on the biomaterial reservoir, more preferably a syringe, will be lessened upon reaching the pleural space.

Figure 14:
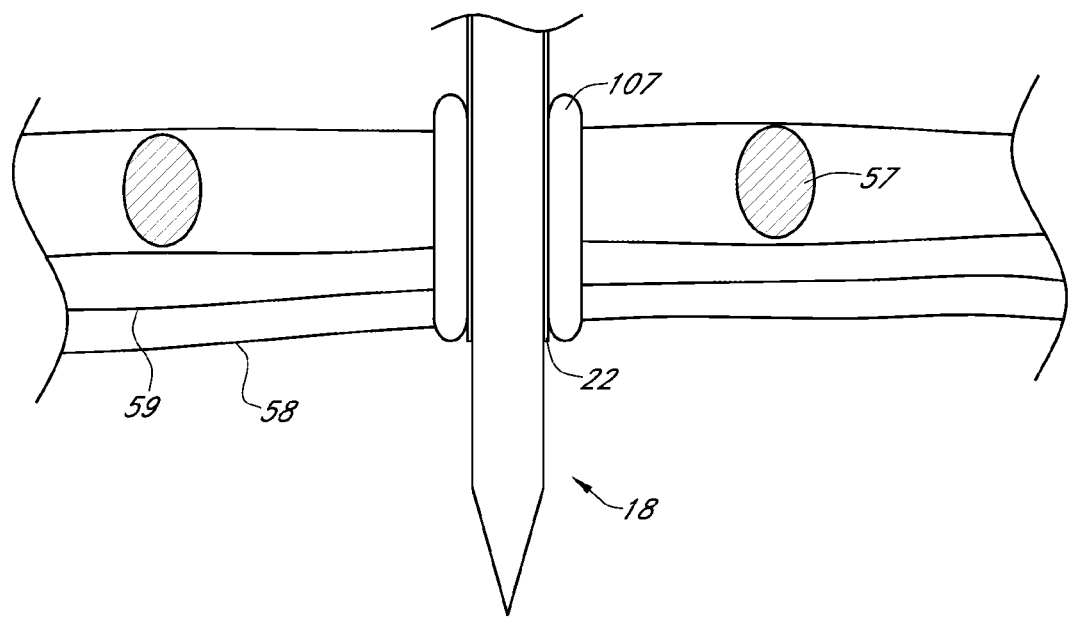
FIG. 14 illustrates an additional embodiment of a device disclosed herein.

FIG. 14 provides another method of sealing using a circumferentially oriented expandable member 107 (chest wall 57, visceral pleura 58, parietal pleura 59). Upon insertion of the tissue introducer 18 and housing sheath 22 (also referred to herein as 19) the expandable members will be expanded once the pleural space has been breached. The expandable members can be attached to the outside of the housing sheath 22 in an unexpanded manner. Upon reaching the pleural space which can be verified via an imaging modality including but not limited to magnetic resonance imaging (MRI), computed tomography (CT) scan, X-Ray, and/or ultrasound the expandable member can be inflated with a fluid including but not limited to air, saline, or other fluid. To inflate the expandable member it would require a valved inlet port (not shown) attached to a fluid delivery line and a reservoir. The reservoir can be activated by an electrical pump or a manual pump such as an inflation bulb as is common on sphygmomanometers. Additionally, the expandable members can be made of a material including but not limited to silicone, PTFE, polyurethanes, polyethylenes, nylons, Dacron, Teflon, plastics, rubbers or other elastic material. The expandable members can be left in place after the procedure has finished and removed after up to 6 hours, 10 hours, 24 hours, 1 week, 1 month or any other suitable time. Additionally, the expandable members can be made of a biodegradable material including poly(glycolic acids) PGA, poly(lactic acids) PLA, and/or copolymers thereof. The expandable members should line the tract from the visceral pleura through the chest wall thereby preventing both external and internal air from entering the pleural space aiding a pneumothorax.

Figure 15:
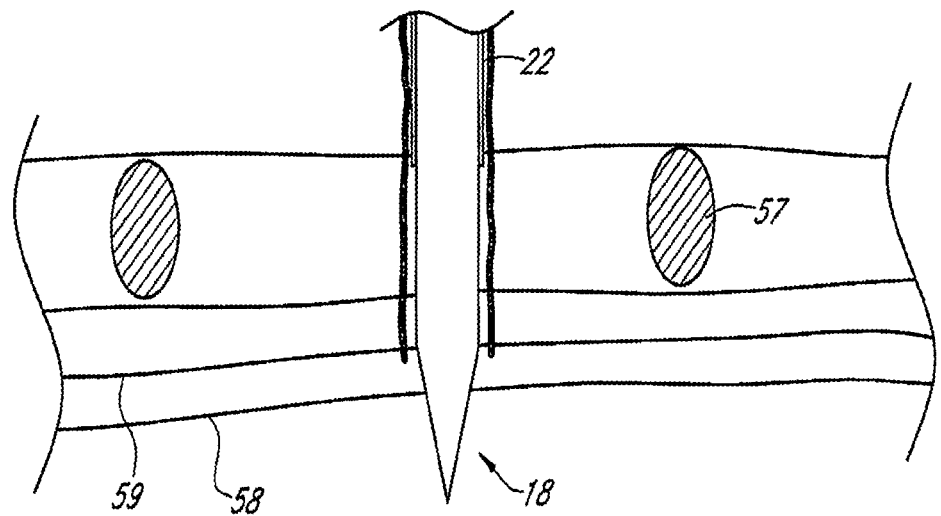
FIG. 15 illustrates an additional embodiment of a device disclosed herein.

FIG. 15 provides another method of sealing comprising a tissue introducer 18 and housing sheath 22 (also referred to herein as 19) and a sealant 23 (chest wall 57, visceral pleura 58, parietal pleura 59). The sealant can be selected from any of the materials listed previously and preferably will react to the pressure, pH, temperature, fluid or other external stimulus which will cause the sealant to line the tract in a more viscous manner and be deposited within the tract effectively preventing fluid from traveling from the chest wall into the lung parenchyma and from the lung parenchyma to the chest wall.

Another aspect of the invention includes a seal that may be formed of a silicone-PTFE combination and supplied within the proximal articulation hub of the trocar. The seal acts as a barrier to both fluids and gases and prevents air or gases from entering or exiting through the trocar. Alternatively, the sealant be composed of additional materials including but not limited to silicone, polyurethane, PTFE, and ePTFE. Additionally, the material can be selectively manufactured to have a varying elasticity allowing for resealability after multiple needle insertions. The septa may include a weakened area, marker, or design to indicate the puncture area. Additionally, the septa material may be physically located within the proximal hub of the trocar or it may be outside of the proximal hub. The septa may also be in combination with a cap which can be clamped, screwed, or placed onto the proximal hub of the trocar. The septa, which can also be referred to as a fluidstatic membrane, serves to at least partially (e.g., about 70% or more), and preferably substantially completely (e.g., about 90% or more), or more preferably completely (e.g., about 100%), prevent fluids and gases including but not limited to air, blood, saline, oxygen, carbon dioxide from entering the lumen of the second needle. Additionally, the membrane provides extra protection against a possible pulmonary air embolus by providing a seal against external air. In some embodiments, this protection is provided without allowing for a pressure change within the tissue. In some embodiments, however, "sealed against external air" does not necessarily mean there is no pressure change or that there is an absolute prevention of the entry or exit of air or gas from the tract in the tissue formed as the device is inserted and/or removed from the same. Furthermore, it is important that the septa conform to the 360-degree circumference of the sealant delivery sheath or tissue introducer or any other structure passing therethrough. Conforming to the entire circumference prevents any fluid from exchanging from the proximal-distal side or distal-proximal side of the septa. This is contrary to certain valves or flaps which are used and known in the art which do not provide a 360 degree circumferential seal thereby allowing fluid exchange from the proximal-distal or distal-proximal side of the septa. The septa in combination with the 97 extruded in the chest wall provides protection against external air flowing around the housing sheath into the pleural space or between the housing sheath and tissue introducer. Protecting the pleural space from exposure to all sources air is crucial in preventing pneumothorax.

When selecting the sealant it may be preferable to use any combination of the materials listed above. Additionally, using the techniques described above, the devices and materials may be used in other parts of the body and other treatment modalities without departing from the scope of the invention. For example, the devices and materials may be used for hemostasis in locations including but not limited to kidney, liver, connective tissue, breast, pancreas, spleen, brain, joints, bladder, prostate, mediastinum, muscle, and gastrointestinal tract. Treatment modalities include but are not limited to filling voids in tissue, repairing needle tracts, and repairing wounds or deformations. Furthermore, the device may be used to prevent complications from percutaneous ablation used to treat lesions in the lung, liver, kidney, brain, or other bodily organs.

The sealant may also include any one of the previously described materials in combination with other additives which may include elastin, fibrin, glycoprotein, liposomes, thrombin, calcium, neuroleptics, vitamins, growth factors, glucocorticosteroids, steroids, antibiotics, antibacterial compounds, bactericidal, bacteriostatic compounds, antiviral compounds, antifungal compounds, antiparasitic compounds, tumoricidal compounds, tumoristatic compounds, toxins, enzyme, enzyme inhibitors, proteins, peptides, minerals, neurotransmitters, lipoproteins, glycoproteins, immunomodulators, immunoglobulins, dyes, radiolabels, radiopaque compounds, fluorescent compounds, fatty acids, polysaccharides, cell receptor binding molecules, anti-inflammatories, antiglaucomic compounds, mydriatic compounds, anesthetics, nucleic acids, and polynucleotides.

In particular, the present invention can be used in combination with a biopsy device to treat or diagnose one or more lobes of the lung such as the right upper lobe, right middle lobe, right lower lobe, left upper lobe, and left lower lobe. As stated previously, the sealant can then be delivered before the procedure, during the procedure, and/or after the procedure.

In some embodiments, the device is inserted into the mammalian tissue via the introducer, thereby forming a tract, and the sealant is deposited within the tract by removing the delivery sheath from the housing exterior. In some embodiments, the device delivers sealant from the sealant reservoir into the sealant delivery sheath lumen to the port and onto the mammalian tissue.

Thus, in some embodiments, this disclosure provides devices configured to deposit a biomaterial within a tissue, the device comprising: a housing comprising a housing exterior, a housing lumen, a housing proximal end, and a housing distal end; an introducer comprising an introducer lumen, an introducer proximal end, and an introducer distal end; the introducer being positioned within the housing lumen; a delivery sheath comprising delivery sheath tabs and at least one folding line, and being positioned around the housing exterior; and, one or more biomaterials between the delivery sheath and the housing exterior. In some embodiments, the at least one folding line is a perforated line extending along the length of the delivery sheath. In some embodiments, each folding line is positioned within the delivery sheath approximately opposite one another. Illustrative embodiments of such devices are shown in FIGS. 3 and 4. In some embodiments, this disclosure also provides kits comprising: a housing comprising a housing exterior, a housing lumen, a housing proximal end, and a housing distal end; and, an introducer comprising an introducer lumen, an introducer proximal end, and an introducer distal end; the introducer being positioned within the housing lumen: a delivery sheath comprising delivery sheath tabs and at least one folding line, and being positioned around the housing exterior; and, one or more biomaterials between the delivery sheath and the housing exterior. In some embodiments, the kits further comprise one or more containers comprising one or more biomaterials that may, and preferably do, comprise one or more sealants. In some embodiments, the one or more containers is a biomaterial reservoir, and can be a syringe (with or without an attached needle). Methods for using such devices and kits are also provided herein. In some embodiments, the methods comprising using the device to expose the biomaterial to the tissue by removing the delivery sheath from around the housing exterior. In some embodiments, the delivery sheath is removed by applying a pulling force to the delivery sheath tabs such that the delivery sheath is removed from the device. In preferred embodiments, the device is inserted into tissue prior to removing the delivery sheath from around the housing exterior. In some embodiments, the tissue is a mammalian tissue, such as preferably, lung parenchyma. In some embodiments, the methods can be used to prevent pneumothorax.

In some embodiments, this disclosure provides devices configured to deposit biomaterial within a tissue, the devices comprising: a housing comprising a housing proximal end, a housing lumen, a housing sheath, and a housing distal end; and, a tissue introducer sheath comprising a tissue introducer sheath lumen, a tissue introducer proximal end, and a tissue introducer distal end comprising an optionally beveled port, and being positioned within the housing lumen. In some embodiments, one or more biomaterial reservoirs comprising one or more biomaterials is in fluid communication with the tissue introducer sheath lumen at the tissue introducer proximal end. In some embodiments, the one or more biomaterials comprises one or more sealants. In some embodiments, each folding line is positioned within the delivery sheath approximately opposite one another. Illustrative embodiments of such devices are shown in FIGS. 6 and 8. In some embodiments, this disclosure provides kits comprising: a housing comprising a housing proximal end, a housing lumen, a housing sheath, and a housing distal end; and, a tissue introducer sheath comprising a tissue introducer sheath lumen, a tissue introducer proximal end, and a tissue introducer distal end comprising an optionally beveled port, and being positioned within the housing lumen. In some embodiments, such kits may comprise one or more biomaterial reservoirs (e.g., a syringe with or without a needle) comprising one or more biomaterials that preferably comprises at least one sealant. In some embodiments, this disclosure also provides methods for using such devices and kits to deliver one or more biomaterials to tissue (e.g., along a device tract within the tissue) through the tissue introducer sheath. In some embodiments, the device is inserted into tissue prior to delivering the biomaterial to the tissue. In some embodiments, the biomaterial is delivered to the tissue as the device is being inserted into tissue and/or as the device is being removed from the tissue. In preferred embodiments, the biomaterial is delivered to the tissue continuously. In some embodiments, the tissue is a mammalian tissue, such as mammalian tissue including lung parenchyma. In some embodiments, these methods can be used to prevent pneumothorax.

In some embodiments, this disclosure provides devices configured for applying a biomaterial to a tissue, the devices comprising: a first needle comprising a first needle closed distal tip (e.g., 84 in FIG. 6A-C) a first needle proximal articulation hub (e.g., 81 in FIGS. 6A-B) comprising a first needle proximal articulation hub coupling mechanism (e.g., the female portion of a luer lock system), wherein the coupling mechanism can include but is not limited to screwing, press-fit, snap-fit, molding, and/or adhesive, and on its distal end, a first needle distal port (e.g., 83 in FIGS. 6A-C) located proximally to the first needle closed distal tip, and a first needle hollow lumen (82A in FIG. 6A) in fluid communication with the first needle distal port and a biomaterial reservoir (e.g., 85 in FIGS. 6A-B); and, a second needle (e.g., 92 in FIG. 6A) comprising: a second needle internal lumen (e.g., 19 in FIG. 6A); a second needle proximal housing comprising (e.g., 21 in FIG. 6A): a second needle septa configured to allow passage of the first needle into the second needle internal lumen without a pressure change from the proximal side to distal side of the membrane (e.g., 110 in FIG. 6F), a second needle proximal housing coupling mechanism (e.g., the corresponding male portion of a luer lock system such as 96 in FIG. 6A), wherein the coupling mechanism can include but is not limited to screwing, press-fit, snap-fit, molding, and/or adhesive, located on the proximal end of the second needle, and a second needle open distal end (e.g., 90 in FIG. 6A); wherein: when the first needle proximal articulation hub coupling mechanism is coupled to the second needle proximal housing coupling mechanism (e.g., 96 in FIG. 6A; coupled 81 and 21 in FIG. 6B), the first needle is positioned within the second needle internal lumen and the first needle distal port is distal to the second needle open distal end (e.g., 19 and 82 in FIG. 6C). In some embodiments, the first needle proximal articulation hub coupling mechanism of such devices is coupled to the second needle proximal housing coupling mechanism. In some embodiments, one or more biomaterial reservoirs comprising one or more biomaterials (e.g., preferably comprising one or more sealants) is in fluid communication with the first needle hollow lumen. In some embodiments, this disclosure provides kits comprising: a first needle comprising a first needle closed distal tip, a first needle proximal articulation hub comprising a first needle proximal articulation hub coupling mechanism on its distal end, a first needle distal port located proximally to the first needle closed distal tip, and, a first needle hollow lumen in fluid communication with the first needle port and a biomaterial reservoir; and, a second needle comprising a second needle internal lumen, a second needle proximal housing comprising a second needle septa (e.g., 110 in FIG. 6F) configured to allow passage of the first needle into the second needle internal lumen without a pressure change from the proximal side to distal side of the membrane, and a second needle proximal housing coupling mechanism located on the proximal end of the second needle; and, a second needle open distal end. In some such kits, the first needle proximal articulation hub coupling mechanism is coupled to the second needle proximal housing coupling mechanism. In some embodiments, the kits comprise one or more biomaterial reservoirs (e.g., a syringe with or without a needle) comprising one or more biomaterials (e.g., preferably one or more sealants).

In some embodiments, this disclosure provides a device for depositing biomaterial within a tissue, the device comprising: a housing comprising a housing proximal end, a housing lumen, a housing sheath, and a housing distal end; and, a tissue introducer positioned within the housing lumen and comprising a tissue introducer lumen, a tissue introducer proximal end, a tissue introducer distal end, and at least one port. In some embodiments, the tissue introducer distal end terminates as a closed tip. In some embodiments, each at least one port is a first opening in the tissue introducer lumen and wherein the tissue introducer lumen does not comprise a second opening opposite the first opening. In some embodiments, the tissue introducer proximal end comprises an articulable hub and the housing proximal end comprises a fastening section. In some embodiments, the articulable hub is configured to be coupled to the fastening section, optionally wherein upon coupling or the articulable hub and the fastening section, the port and distal end of the tissue introducer are positioned distal of the housing distal end. In some embodiments, the port is in fluid communication with a biosealant reservoir, optionally wherein the biosealant reservoir comprises a syringe. In some embodiments, the housing distal end is angled wherein one side of the housing wall is longer than an opposite side of the housing wall. In some embodiments, the tissue introducer is positioned within the housing lumen, the longer side of the housing is located directly opposite the port. In some embodiments, the tissue introducer proximal end comprises a body portion configured for gripping, which can be in the form of ridge or dots located on the body portion. In some embodiments, the body portion is configured to indicate the orientation of the housing distal end to a user and/or to indicate the orientation of the port to a user. In some embodiments, a bulbous housing can be attached to the proximal end of the body portion. In some embodiments, a septa (which can also be referred to as a one-way hemostatic valve) is located in between the bulbous housing and body portion. In some embodiments, the bulbous housing is made of a transparent material configured to allow visualization of fluid within the bulbous housing. In some embodiments, the tissue introducer can be configured to pierce through the septa when the tissue introducer is positioned within the housing lumen. In some embodiments, such as when the tissue introducer has pierced the septa, the septa provides a circumferential seal around the entire tissue introducer lumen.

This disclosure also provides methods for using such devices and kits. In some embodiments, the methods comprise delivering the biomaterial to the tissue through the first needle hollow lumen. In some embodiments, the device is inserted into tissue prior to delivering the biomaterial to the tissue. In some embodiments, the biomaterial is delivered to the tissue as the device is being inserted into tissue and/or as the device is being inserted into the tissue and as the device is being removed from the tissue. In some embodiments, and preferably, the biomaterial is delivered to the tissue continuously. In some embodiments, the tissue is a mammalian tissue, such as preferably that comprising lung parenchyma. In some embodiments, the methods can be used to prevent pneumothorax.

In some embodiments, the devices provided herein may include a port comprising one or more than one holes, the more than one holes being optionally of different sizes and/or oriented at different angles relative to one another.

In some embodiments, the biomaterial included with or use with the devices described herein can comprise at least one component selected from the group consisting of hydrogel; polymer; human biologic material; gel; glue; adhesive; a microsphere; a composition comprising a cross-linker, a material that swells in reaction to a stimuli optionally selected from the group consisting of pH, fluid, blood, saline, temperature, light, electron-beam, gamma-radiation, ultraviolet light, deoxyribonucleic acid (DNA), an initiator, adhesiveness, viscosity, density, hardness, and flexibility; and combinations of the same. In some embodiments, the biomaterial reservoir(s) included with or use with the devices described herein comprises a fluid injection mechanism. In some embodiments, the housing proximal end or second needle proximal housing comprises a one-way hemostatic valve (which may also be referred to as a septa).

In some embodiments, this disclosure provides methods comprising step a) of inserting into and advancing through a tissue a device described herein thereby forming a device tract, and continuously depositing biomaterial into the device tract as the device is inserted into and advanced through the tissue. In some embodiments, such methods may comprise any one or more additional steps of: b) prior to step a), performing steps a1) of locating a target site in a tissue; and a2) verifying that the device is on a correct trajectory to the target site, wherein: 1) if the device is not on a correct trajectory to the target site, retracting the device from the device tract while continuously depositing biomaterial into the device tract, and repeating step a1) and a2) until the device is determined to be on a correct trajectory to the target site; or, 2) if the device is on a correct trajectory to the target site in step c), advancing the device toward the target site while continuously depositing biomaterial into the device tract; d) removing the tissue introducer sheath from the housing lumen, or removing the first needle from the internal lumen of the second needle; e) inserting a biopsy tool into the housing lumen or internal lumen of the second needle and removing a biopsy sample from the tissue; f) verifying the biopsy sample is adequate; g) removing the biopsy tool from the internal lumen of the second needle; h) inserting the tissue introducer sheath into the housing lumen, or inserting first needle into the internal lumen of the second needle, and continuously depositing biomaterial into the device tract as the tissue introducer sheath or first needle is inserted into and advanced through the housing lumen or internal lumen of the second needle, respectively; and, i) performing post-procedure imaging to check for complications. In some embodiments, the methods comprise each of steps a) through i). In some embodiments, this disclosure provides method for applying a biomaterial, optionally a biosealant, to a tissue using a biosealant delivery assembly comprising: a) a housing component comprising a housing proximal end, a housing lumen, a housing sheath, and a housing distal end; and, b) a tissue introducer component comprising a tissue introducer lumen, a tissue introducer proximal end, a tissue introducer distal end, and a port; wherein the biomaterial is deposited onto the tissue through the port. In some embodiments, the biosealant delivery assembly is inserted into the tissue prior to delivering the biomaterial to the tissue, as the biosealant delivery assembly is being inserted into tissue, and/or as the biosealant delivery assembly is being removed from the tissue. In illustrative embodiments, devices that can be used in such methods are illustrated in FIGS. 6A-F and 8. In some embodiments, the one or more biomaterials comprises one or more sealants. In some embodiments, the tissue is mammalian tissue, e.g., preferably comprising lung tissue such as the lung parenchyma. In preferred embodiments, the delivery of sealant to the device tract and especially the lung tissue prevents air from entering or exiting the lung. In some embodiments, the methods can be used to prevent pneumothorax.

In some embodiments, this disclosure provides methods for making a sealant delivery device assembly or a component thereof by: a) producing a housing sheath component (92) comprising a housing proximal end (21) comprising a housing opening (94), a housing sheath (19) surrounding a housing lumen, and a housing distal end (90); and/or, b) producing a tissue introducer component (82) comprising a tissue introducer lumen (82A), a tissue introducer proximal end (80), an articulable hub (81), one or more ports (83), and a tissue introducer distal end (84); and, to make a sealant delivery device assembly, c) reversibly connecting the housing sheath component (92) and the tissue introducer component (82), wherein said the tissue introducer component (82) is positioned within the housing sheath component (92) such that the tissue introducer lumen (82A) being surrounded by housing sheath (19) wherein at least one of said one or more ports (83) and the tissue introducer distal end (84) protrude from the housing distal end (90). In some such embodiments, the housing sheath component (92) and the tissue introducer component (82) are reversibly connected to one another using a luer lock arrangement. In some such embodiments, the housing proximal end (21) comprises a bulbous housing (112) comprising a bulbous housing lumen, a body (97) comprising a body lumen, and a hub (97B), optionally one or more grips (97A) on the exterior of body (97), a septa (110) at least partially separating the bulbous housing (112) and the body (97) and separating the bulbous housing lumen and the body lumen. In some such embodiments, the housing proximal end (21) is produced by: a) producing the bulbous housing (112) comprising a bulbous housing lumen, the body (97) comprising a body lumen, and the septa (110); b) positioning the septa (110) into a receiving surface of the body (97), and positioning the bulbous housing (112) upon the body (97) and septa (110). In some embodiments, the housing sheath component (92) and/or the tissue introducer component (82), and/or a component thereof, optionally the septa (110), is produced using 3D printing.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

EXAMPLES

Figure 13:
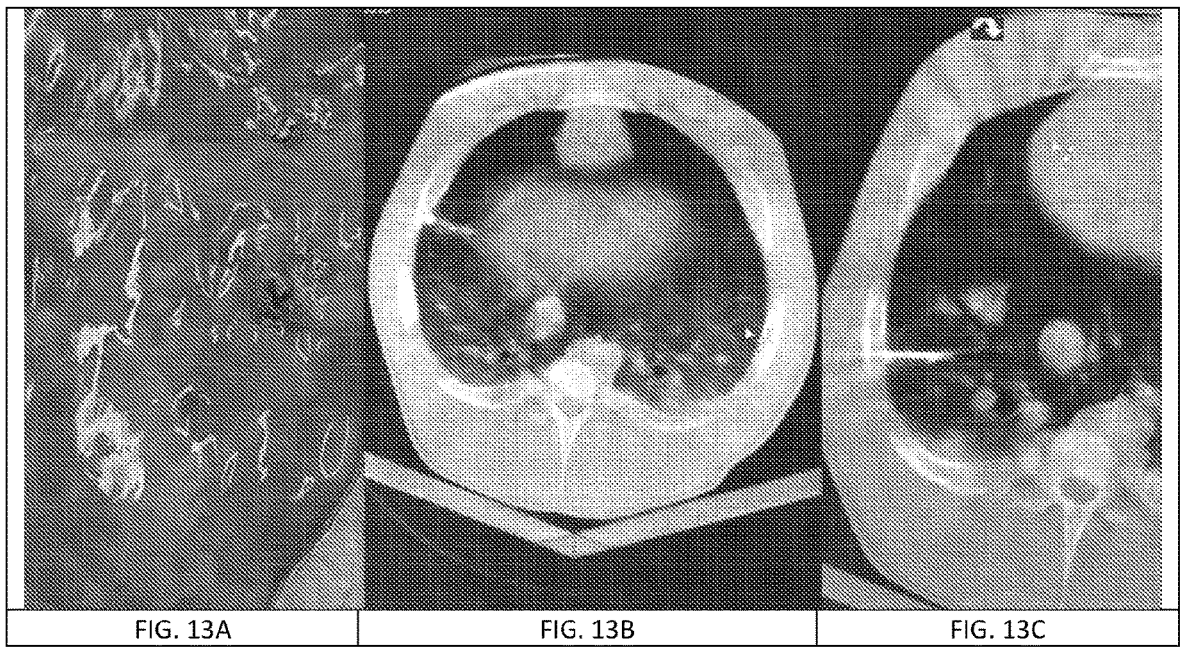
FIGS. 13A-C illustrate in vivo results obtained using a device disclosed herein.

FIGS. 13A-13C portray images taken during a swine study with the proposed device.

FIG. 13A is a portrayal of the swine lung tissue after necropsy. The figure emphasizes that multiple needle insertion points can be used and the tract can be successfully sealed before, during, and/or after the biopsy occurs. This greatly reduces the risk of a pneumothorax occur because there is no open tract leading to the pleural space.

FIG. 13B is a CT-image taken post-procedurally in which the radiopaque line reflects a chitosan-genipin biosealant which was infused with radiopaque particles. The line shows that there is a seal which extends from the lesion to the pleural space and through the chest wall thereby ensuring fluids or gases are blocked from traveling up the tract into the pleural space or tumor cells cannot travel up the needle tract due to the presence of a biosealant.

FIG. 13C is a CT-image taken post-procedurally in which the radiopaque line reflects a chitosan-genipin biosealant which was infused with radiopaque particles. The line shows that there is a seal which extends from the lesion to the pleural space and through the chest wall thereby ensuring fluids or gases are blocked from traveling up the tract into the pleural space or tumor cells cannot travel up the needle tract due to the presence of a biosealant.

Target site was located in the right lower lobe of a swine lung (FIG. 13B). Device (consisting of an 18.5 gauge second needle and a 20 gauge first needle used to deliver the biosealant) was advanced through the anterior side while injecting biosealant in the chest wall, pleural space, and lung parenchyma until it was located within the lung. A CT-image was then taken to verify the device was on the correct trajectory to the target site. Due to user dissatisfaction the device was fully retracted while applying biosealant along the tract. Once fully retracted, the device was then inserted along another trajectory while continuously applying biosealant resulting in a different chest wall, pleural layer, and lung tissue puncture site. FIG. 13A shows that multiple needle insertion sites were performed and the tract was effectively sealed after retraction. Once located at the desired target site the first needle was removed and a biopsy sample was taken using a standard 20 gauge biopsy gun, this was repeated three times. After the biopsy samples, the first needle was reinserted into the second needle and the device was retracted out of the swine while continuously injecting biosealant.

An immediate post-procedure CT-image was then taken confirming no pneumothorax was present and the biosealant was continuous between the chest wall, pleural layers, and target site within the lung tissue (FIG. 13B).

A second biopsy was then performed wherein the device was inserted through the posterior side of the swine into the right lung (FIG. 13C). The target site was located in the right upper lobe and a path crossing the juncture between the right middle lobe and right upper lobe, also known as a fissure, was selected. Upon insertion through the chest wall, pleural layers, and lung tissue a CT-image was taken to ensure device trajectory would intercept the target site. Trajectory was confirmed and the device was advanced while applying biosealant until it was located at the target site. Once located at the desired target site the first needle was removed and a biopsy sample was taken using a standard 20 gauge biopsy gun, this was repeated three times. After the biopsy samples, the first needle was reinserted into the second needle and the device was retracted out of the swine while continuously injecting biosealant.

An immediate post-procedure CT-image was then taken (FIG. 13C) confirming no pneumothorax was present and the biosealant was continuous between the chest wall, pleural layers, and target site within the lung tissue. Additionally, the imaging verified that the biosealant was continuous across the intralobular fissure.

What is claimed is:

1. A device for depositing a material within a tissue, the device comprising:
    a housing comprising a housing proximal end, a housing sheath, and a housing distal end; and,
    a tissue introducer positioned within the housing sheath, the tissue introducer comprising:
        a tissue introducer proximal end,
        a tissue introducer distal end comprising one or more ports located on the side wall of the tissue introducer, and,
        a longitudinal lumen comprising a distal end comprising the one or more ports.

2. The device of claim 1 wherein when the tissue introducer proximal end comprises an articulatable hub.

3. The device of claim 1 wherein the longitudinal lumen extends from the tissue introducer proximal end to the closed distal tip.

4. The device of claim 3 wherein the closed distal tip is configured to pierce tissue.

5. The device of claim 3 wherein the one or more ports are located on the longitudinal lumen.

6. The device of claim 5 wherein the one or more ports comprises at least two ports or at least three ports.

7. The device of claim 1 wherein the articulatable hub comprises a luer lock attachment configured to receive a syringe.

8. The device of claim 1 wherein the one or more ports are configured to allow sealant to flow from the inside of the tissue introducer to an external environment.

9. The device of claim 1 wherein when the tissue introducer is positioned within the housing sheath and the housing sheath completely encircles the tissue introducer.

10. The device of claim 2 wherein the closed distal tip comprises a (i) single bevel tip (ii) multi-bevel tip.

11. The device of claim 1 wherein the material is a sealant.

12. A device for depositing a material within a tissue, the device comprising a tissue introducer, wherein:
    the tissue introducer comprises a tissue introducer proximal end, a longitudinal lumen, one or more ports, and a closed distal tip;
    the tissue introducer proximal end comprises an articulatable hub in which the articulatable hub comprises a luer lock connection configured to receive a syringe;
    the longitudinal lumen extends from the tissue introducer proximal end to the closed distal tip;
    the one or more ports are located distal to the tissue introducer proximal end and the one more ports comprise at least two ports located on the longitudinal lumen; and,
    the one or more ports are configured to allow a sealant material to flow from inside the tissue introducer lumen to the outside environment.

13. The device of claim 11 wherein the material is a sealant.

* * * * *